United States Patent
Mitrani et al.

(10) Patent No.: US 12,213,994 B2
(45) Date of Patent: Feb. 4, 2025

(54) COMPOSITIONS AND METHODS FOR TREATING PAIN WITH EXTRACELLULAR VESICLES

(71) Applicant: Organicell Regenerative Medicine, Inc., Miami, FL (US)

(72) Inventors: Maria Ines Mitrani, Miami Beach, FL (US); Michael Bellio, Miami, FL (US); Albert Mitrani, Miami, FL (US)

(73) Assignee: Zeo ScientifiX, Inc., Fort Lauderdale, FL (US)

( * ) Notice: Subject to any disclaimer, the term of this patent is extended or adjusted under 35 U.S.C. 154(b) by 0 days.

(21) Appl. No.: 18/063,227

(22) Filed: Dec. 8, 2022

(65) Prior Publication Data

US 2023/0277588 A1    Sep. 7, 2023

Related U.S. Application Data

(60) Provisional application No. 63/287,466, filed on Dec. 8, 2021.

(51) Int. Cl.
| | | |
|---|---|---|
| *A61K 35/14* | (2015.01) | |
| *A61K 9/00* | (2006.01) | |
| *A61K 9/127* | (2006.01) | |
| *A61K 47/64* | (2017.01) | |
| *A61P 19/02* | (2006.01) | |
| *A61P 29/00* | (2006.01) | |

(52) U.S. Cl.
CPC ............ *A61K 35/14* (2013.01); *A61K 9/0014* (2013.01); *A61K 9/127* (2013.01); *A61K 47/6425* (2017.08); *A61P 19/02* (2018.01); *A61P 29/00* (2018.01)

(58) Field of Classification Search
None
See application file for complete search history.

(56) References Cited

U.S. PATENT DOCUMENTS

| | | |
|---|---|---|
| 2017/0100439 A1 | 4/2017 | Harrell |
| 2018/0250343 A1 | 9/2018 | Reems et al. |
| 2019/0290696 A1* | 9/2019 | De Miroschedji ...... A61P 25/00 |
| 2020/0179827 A1 | 6/2020 | Deregibus et al. |
| 2020/0264185 A1 | 8/2020 | Xu et al. |
| 2020/0289583 A1 | 9/2020 | Ferreira et al. |

FOREIGN PATENT DOCUMENTS

| | | |
|---|---|---|
| WO | WO2013082487 | 6/2013 |
| WO | WO 2017/003954 A1 | 1/2017 |
| WO | WO 2017/165698 A1 | 9/2017 |

OTHER PUBLICATIONS

Of Usman et al (Nature Communications, 2018, 9:2359, 1-15). (Year: 2018).*
Malda et al (Nat Rev Rheumatol, 2016, 12(4), 243-9). (Year: 2016).*
Achari et al., Adiponectin, a Therapeutic Target for Obesity, Diabetes, and Endothelial Dysfunction. Int J Mol Sci. Jun. 21, 2017;18(6):1321(17 pages).
Arend, The balance between IL-1 and IL-1Ra in disease. Cytokine Growth Factor Rev. Aug.-Oct. 2002;13(4-5):323-40.
Dixon et al., Amniotic Fluid Exosome Proteomic Profile Exhibits Unique Pathways of Term and Preterm Labor. Endocrinology. May 1, 2018;159(5):2229-2240.
Hovius et al., The urokinase receptor (uPAR) facilitates clearance of Borrelia burgdorferi. PLoS Pathog. May 2009;5(5):e1000447 (14 pages). Epub May 22, 2009.
Johns et al., Growth factor effects on costal chondrocytes for tissue engineering fibrocartilage. Cell Tissue Res. Sep. 2008;333(3):439-47. Epub Jul. 3, 2008.
Koike et al., Characterization of amniotic stem cells. Cell Reprogram. Aug. 2014;16(4):298-305.
Liu et al., The cytokine storm of severe influenza and development of immunomodulatory therapy. Cell Mol Immunol. Jan. 2016;13(1):3-10. Epub Jul. 20, 2015.
Murphy et al., Isolation, cryopreservation and culture of human amnion epithelial cells for clinical applications. J Vis Exp. Dec. 21, 2014;(94):52085(8 pages).
Reiter et al., Stromal derived factor-1 mediates the lung regenerative effects of mesenchymal stem cells in a rodent model of bronchopulmonary dysplasia. Respir Res. Jul. 12, 2017;18(1):137(11 pages).
Wu et al., Risk Factors Associated With Acute Respiratory Distress Syndrome and Death in Patients With Coronavirus Disease 2019 Pneumonia in Wuhan, China. JAMA Intern Med. Jul. 1, 2020;180(7):934-943. Erratum in: JAMA Intern Med. Jul. 1, 2020;180(7):1031.
Xie et al., The relationship between amniotic fluid miRNAs and congenital obstructive nephropathy. Am J Transl Res. Apr. 15, 2017;9(4):1754-1763.
Antounians et al., Antounians et al. (2019) Scientific Reports 9: (11 pages) (year: 2019), Feb. 12, 2019.
Balbi et al., Balbi et al. (2017) Stem Cells Transitional Medicine 6: 1340-1355. (Year: 2017), Mar. 8, 2017.
Bazrafshan et al., Bazrafshan et al. (2014) J. Surg. Res. 188: 545-552 (Year: 2014), Jan. 29, 2014.

(Continued)

*Primary Examiner* — Celeste A Roney
(74) *Attorney, Agent, or Firm* — W. John Eagan; Malloy & Malloy, P.L.

(57) ABSTRACT

Described herein are cell-free therapeutic compositions derived from blood or plasma and uses thereof for the treatment of selected diseases and disorders.

30 Claims, 5 Drawing Sheets
(2 of 5 Drawing Sheet(s) Filed in Color)

(56) References Cited

OTHER PUBLICATIONS

Herretes et al., Herretes et al. (2006) American J. Ophthmology Aug. 2006: 271-278 (Year: 2006), Aug. 1, 2006.
Sheller-Miller et al., Sheller-Miller et al. (2020) Methods in Enzymology, vol. > 645: 181-194. (Year: 2020), Jul. 6, 2020.
C. Luke Dixon et al., Amniotic fluid exosome proteomic profile exhibits unique pathways of term and preterm labor; Endocrinology, vol. 159, No. 5, pp. 2229-2240, Apr. 4, 2018.
Manuela Zavatti et al., Comparison of the therapeutic effect of amniotic fluid stem cells and their exosomes on monoiodoacetate-induced animal model of osteoarthritis; BioFactors, vol. 46, No. 1, pp. 106-117, Oct. 18, 2019.
Juntao Xie et al., The relationship between amniotic fluid miRNAs and congenital obstructive nephropathy; Am J Transl Res, vol. 9, No. 7, pp. 1754-1763, Apr. 30, 2017.

\* cited by examiner

CD41a EV Capture

CD63 EV Capture

COMPOSITIONS AND METHODS FOR TREATING PAIN WITH EXTRACELLULAR VESICLES

CROSS REFERENCE TO RELATED APPLICATIONS

This application claims priority to and the benefit of U.S. Provisional Patent Application No. 63/287,466, filed on Dec. 8, 2021, and entitled "METHOD OF TREATING PAIN IN A PATIENT COMPRISING THE USE OF EXTRACELLULAR VESICLES". The entire contents of the above-referenced application are incorporated herein by reference.

BACKGROUND

Acute or chronic pain, for example, joint pain is a major factor affecting quality of life. In some instances, depending on which joint is the cause of pain, said pain frequently limits and in some cases completely disables movements or performance daily tasks. For example, pain in a joint in a leg, e.g., the hip, knee, or ankle, limits the patient's ability to move the leg and prevents not only strenuous activities, such as running or jumping, but even routine tasks, such as walking or ascending or descending stairs.

A common source of pain is osteoarthritis. Osteoarthritis (OA) is the most common form of arthritis and occurs most frequently in the hands, hips, and knees. OA is a degenerative joint disease as it occurs when the protective cartilage that cushions the ends of the bones wears down over time, and the underlying bone begins to change. The damage to the joints is irreversible, and therapies are generally focused on the treatment of symptoms, such as inflammation and pain.

SUMMARY

In certain aspects, provided herein is a composition comprising blood-derived nanoparticles. In certain aspects, the nanoparticles are extracellular vesicles (EVs) that are autologous to the subject and include exosomes. In certain aspects, the concentration of the nanoparticles is at least $10^7$ EVs per mL and the nanoparticles have a diameter greater than 20 nm. In certain aspects, the composition includes a protein concentration of at least 0.02 mg/mL.

Also, described in this specification is a method of treating joint pain in a subject in need thereof, comprising administering to the subject a therapeutically effective amount of a composition comprising blood-derived nanoparticles that are autologous to the subject, wherein the nanoparticles have a diameter less than 200 nm, and wherein the joint pain is derived from arthritis. In certain aspects, the arthritis is osteoarthritis or rheumatoid arthritis.

BRIEF DESCRIPTION OF THE DRAWINGS

Novel features of the technologies described in this specification are set forth with particularity in the appended claims. A better understanding of the features and advantages of the present invention will be obtained by reference to the following detailed description that sets forth illustrative implementations, in which the principles of the invention are utilized, and the accompanying drawings (also "Figure" and "FIG." herein). The patent or application file contains at least one drawing executed in color. Copies of this patent or patent application publication with color drawing(s) will be provided by the Office upon request and payment of the necessary fee.

FIG. 1A is a graph showing size distribution of a representative PPX product. FIG. 1B is a bar graph showing average concentration of representative PPX products. FIG. 1C is a bar graph showing average mode size of nanoparticles in representative PPX. In FIGS. 1B-1C, error bars represent standard error of the mean.

FIG. 2A shows an ExoView® analysis of PPX with CD41a capture plates and fluorescent analysis of CD63+, CD81+, and CD9+ nanoparticles. FIG. 2B shows an ExoView® analysis of PPX with CD63 capture plates and fluorescent analysis of CD63+, CD81+, and CD9+ nanoparticles. FIG. 2C is a bar graph showing approximated number of CD41a+ nanoparticles in 3 independent PPX products.

FIG. 4A is a circle chart showing an exemplary representative distribution of various RNA subtypes in PPX. FIG. 4B is a Venn diagram showing an exemplary comparative analysis of representative PPX products indicating about 860 reproducibly detected miRNA.

FIG. 5A shows individual WOMAC scores for study patients at baseline, 6 weeks, and 3 months. FIG. 5B shows mean WOMAC scores for all study subjects at baseline, 6 weeks, and 3 months (±SD).

FIG. 6A shows WOMAC scores of the subjects treated with PPX by IV administration at baseline, 6 weeks, and 3 months. FIG. 6B shows WOMAC scores of those subjects treated with PPX by IA administration at baseline, 6 weeks, and 3 months.

DESCRIPTION

Figure 1A:
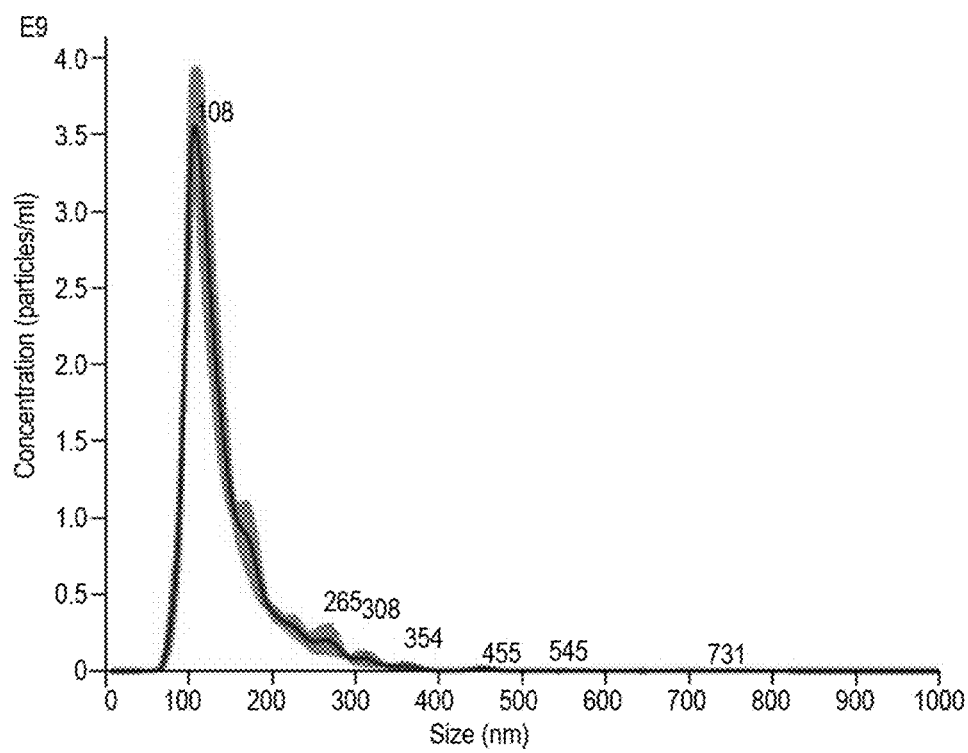
FIGS. 1A-1C present exemplary results of nanoparticle tracking analysis of Patient Pure X (PPX).

Extracellular vesicle (EVs) are cell-derived nanoparticles that contain protein and genetic components with therapeutic properties. EVs are typically sourced from in vitro cell conditioned media or from allogenic biological fluids for use as a therapeutic agent [1]. As used herein, the term "substantially" is intended to have the meaning commonly understood by those of skill in the art to which this invention pertains.

Described in this specification are technologies including compositions derived from autologous whole blood. These compositions include extracellular vesicles (EVs) sourced from a subject's or patient's peripheral circulation, such as platelets. Platelets and plasma are commonly used as a cell source and/or biological fluid source for therapeutic growth factors and secreted factors [2]. Preparations of cleaned, platelet-derived EVs sourced from blood plasma, however, have not yet been used as a therapeutic source of EVs for pain management. Described in this specification are presented are compositions including EV's and methods of manufacturing the same, as well as use of said compositions for pain management.

Compositions

Described in this specification are certain blood-derived compositions including therapeutic compositions. The therapeutic compositions provided herein are distinctly different from naturally occurring blood in both content and function. In some implementations, a therapeutic composition is cell-free or is substantially free of cells. Accordingly, in certain implementations, a therapeutic composition does not contain a eukaryotic cell or a prokaryotic cell. In some implementations, a therapeutic composition contains fewer than three eukaryotic cells and/or prokaryotic cells.

In certain implementations, a therapeutic composition does not contain a pathogen, non-limiting examples of which include a virus, a bacterium, a fungus, a yeast, or a parasite. In certain implementations, a therapeutic composition does not contain a virus.

In some implementations, a therapeutic composition as described in this specification is or includes a blood-derived composition. In certain implementations, a blood-derived composition is a composition that is processed to remove one or more of cells and/or macroparticles (e.g., particles greater than 400 nm, greater than 300 nm or greater than 200 nm in diameter). In some implementations, a blood-derived composition is substantially or completely free of cells and/or macroparticles. In some implementations, a blood-derived composition is substantially free of nanoparticles. In certain implementations, a blood-derived composition is a plasma-derived composition. In certain implementations, a blood-derived composition is derived from filtered blood. In certain implementations, a blood-derived composition is derived from filtered autologous blood. In certain implementations, a blood-derived composition is derived from filtered heterologous blood.

In some implementations, a blood-derived composition is blood or plasma that is filtered through a filter having a pore size of 0.2 um or larger, or 0.1 um or larger, or 0.05 um or larger. In some implementations, a blood-derived composition is blood or plasma that is filtered through a filter having a pore size of 0.05 um to 1 um, 0.1 um to 1 um, 0.2 um to 1 um, 0.05 um to 0.2 um, 0.05 um to 0.5 um, or 0.2 um to 0.5 um. In certain implementations, a blood-derived composition is blood that is subjected to centrifugation at 100×g to 2500×g, or 200×g to 2000×g for a suitable period of time to separate blood from plasma. In certain implementations, plasma is collected and subjected to centrifugation at 80,000×g to 150,000×g for a suitable period of time to precipitate a nanoparticle fraction. In certain implementations, the nanoparticle fraction is resuspended and filtered through a filter having a pore size of 0.1 um or larger, or 0.2 um or larger. In certain implementations, the filter is a 0.22 um filter.

In some implementations, different methods can be used to isolate or concentrate nanoparticles fraction from blood, plasma, or acellular plasma. In some implementations, after plasma separation, the nanoparticles can be extracted and/or concentrated using techniques such as tangential flow filtration, size exclusion chromatography, differential ultracentrifugation, polymeric precipitation, and/or anion-exchange chromatography followed by resuspension.

In some implementations, a blood-derived composition as described in this specification is an autologous blood-derived composition. Accordingly, the blood-derived composition is derived from the blood (or plasma) of the same subject to which the composition is or will be administered. In some implementations, a blood-derived composition is a heterologous blood-derived composition. Accordingly, the blood-derived composition is derived from the blood (or plasma) of a different subject to which the composition is or will be administered.

In some implementations, a therapeutic composition as described in this specification includes nanoparticles. In some implementations, a therapeutic composition as described in this specification includes blood-derived nanoparticles. In some implementations, a therapeutic composition includes 1% to 50% (vol/vol) nanoparticles. In some implementations, a therapeutic composition as described in this specification includes 1% to 40%, 1% to 30%, 1% to 25%, 5% to 40%, 5% to 30%, 5% to 25%, or 10% to 40% (vol/vol) nanoparticles.

In some implementations, a therapeutic composition as described in this specification includes at least $1 \times 10^8$, at least $1 \times 10^9$, at least $1 \times 10^{10}$, at least $1 \times 10^{11}$, at least $2 \times 10^{11}$, at least $4 \times 10^{11}$, at least $5 \times 10^{11}$, at least $1 \times 10^{12}$, at least $5 \times 10^{12}$ or at least $10^{13}$ particles/ml. In some implementations, a therapeutic composition as described in this specification includes a mean, average or absolute amount of nanoparticles in a range of $1 \times 10^8$ to $1 \times 10^{20}$ particles/ml. In some implementations, a therapeutic composition as described in this specification includes a mean, average, or absolute amount of nanoparticles in a range of $1 \times 10^8$ to $1 \times 10^{18}$, $1 \times 10^9$ to $1 \times 10^{18}$, $1 \times 10^{10}$ to $1 \times 10^{18}$, $1 \times 10^{11}$ to $1 \times 10^{18}$, $1 \times 10^{12}$ to $1 \times 10^{18}$, $1 \times 10^{13}$ to $1 \times 10^{18}$, $1 \times 10^{14}$ to $1 \times 10^{18}$, $1 \times 10^{12}$ to $1 \times 10^{16}$, $1 \times 10^{12}$ to $1 \times 10^{15}$, $1 \times 10^{12}$ to $1 \times 10^{15}$, $1 \times 10^{11}$ to $1 \times 10^{16}$, $1 \times 10^{11}$ to $1 \times 10^{14}$, or $1 \times 10^{11}$ to $1 \times 10^{13}$, or $1 \times 10^{10}$ to $1 \times 10^{13}$ (particles/ml). In some implementations, a therapeutic composition as described in this specification includes a mean, average, or absolute amount of nanoparticles in a range of $1 \times 10^8$ to $1 \times 10^{13}$ or $1 \times 10^8$ to $1 \times 10^{12}$ particles/ml. In some implementations, a therapeutic composition as described in this specification includes a mean, average, or absolute amount of nanoparticles in a range of $1 \times 10^{11}$ to $1 \times 10^{13}$, $4 \times 10^{11}$ to $1 \times 10^{13}$, $5 \times 10^{11}$ to $1.5 \times 10^{12}$, $4 \times 10^{11}$ to $1.1 \times 10^{12}$, or $5.0 \times 10^{10}$ to $5.0 \times 10^{12}$, or $1 \times 10^{10}$ to $1 \times 10^{13}$ particles/ml. In some implementations, a therapeutic composition as described in this specification includes a mean, average, or absolute amount of nanoparticles in a range of about $1 \times 10^{10}$ to $1 \times 10^{13}$ particles/ml. In some implementations, a therapeutic composition as described in this specification includes a mean, average, or absolute amount of nanoparticles in a range of about $5.0 \times 10^{10}$ to $5.0 \times 10^{12}$ particles/ml.

In some implementations, a therapeutic composition as described in this specification includes one or more proteins. In some implementations, a therapeutic composition as described in this specification includes one or more cytokines, soluble receptors and/or growth factors selected from the cytokines, soluble receptors and growth factors. In some implementations, a therapeutic composition as described in this specification includes one or more cytokines, soluble receptors and/or growth factors that are typically present in the blood or plasma. In some implementations, a therapeutic composition as described in this specification includes one or more cytokines, soluble receptors and/or growth factors that are typically present in blood. In some implementations, a therapeutic composition as described in this specification includes one or more cytokines, soluble receptors and/or growth factors that are typically present in plasma. In some implementations, a therapeutic composition as described in this specification includes one or more cytokines, soluble receptors and/or growth factors that are typically present in the human blood or plasma. In some implementations, a therapeutic composition as described in this specification includes one or more cytokines, soluble receptors and/or growth factors that are typically present in human blood. In some implementations, a therapeutic composition as described in this specification includes one or more cytokines, soluble receptors and/or growth factors that are typically present in human plasma. In some implementations, a therapeutic composition as described in this specification includes one or more cytokines, soluble receptors and/or growth factors, non-limiting examples of which include angiogenin (ANG), BLC, EGF (epidermal growth factor), FGF-6 (fibroblast growth factor 6), GCP-2 (CXCL6), IGFBP-1 (Insulin Like Growth Factor Binding Protein 1), IGF-BP2 (Insulin Like Growth Factor Binding Protein 2), IGF-BP4 (Insulin Like Growth Factor Binding Protein 4), IL-1RA (Interleukin 1 Receptor Antagonist), IL-6, LEPTIN, MCP-1 (CCL2), MIG (CXCL9), MIP-1DELTA, NAP-2, adiponectin (ACRP30), GRO-A, HCC-4, HGF, ICAM-1, IGFBP-6, IL-1β, IL-1R4, IL-6R, IL-8, IL-10, IFNγ, TNFα, OPG, sTNFRII, sTNFRI, TIMP-1, TIMP-2, and UPAR. In some implementations, a therapeutic composition as described in this specification includes one or more proteins typically found in human blood or plasmas, non-limiting examples of which include adhesive proteins such as Von Willebrand factor, fibrinogen, trombospondi-1, trombospondin-2, and laminin-8); growth factors such as Epidermal growth factor (EGF), insulin-like growth factor 1 (IGF-1), hepatocyte growth factor (HGF), and transforming growth factor β (TGF-β); angiogenic factors such as Vascular endothelium growth factor (VEGF), platelet-derived growth factor (PDGF), and fibroblast growth factor (FGF); chemokines such as CCL5 (RANTES), CCL-3 (MIP-1a), CCL-2 (MCP-1), CCL-7 (MCP-3), CXCL8 (IL-8), CXCL2 (MIP-2), CXCL6 (LIX), CXCL-1 (GRO-a), CXCL5 (ENA-78), CXCL-12 (SDF-1a), and CXCL4 (PF4); clotting factors and their inhibitors such as Factor V, factor IX, antithrombin, factor S, protease nexin-1, protease nexin-2, and tissue factor pathway inhibitor; integral membrane proteins such as aIIb3, GPIba-IX-V, GPVI, TLT-1, and p-selectin; and immune mediators such as Complement C3 precursor, complement C4 precursor, factor D, factor H, C1 inhibitor, and IgG.

In some implementations, a therapeutic composition as described in this specification includes a protein, a cytokine or a growth factor that is derived from or naturally found in blood. In some implementations, a therapeutic composition as described in this specification includes a protein, a cytokine, or a growth factor that is recombinantly produced. In some implementations, a therapeutic composition as described in this specification includes a protein, a cytokine, or a growth factor that is expressed, produced, isolated, and/or purified from a non-human source.

In some implementations, a therapeutic composition as described in this specification includes an amount of protein of at least 0.001 mg/mL, at least 0.01 mg/mL, at least 0.02 mg/mL, at least 0.03 mg/mL, at least 0.04 mg/mL, at least 0.05 mg/mL, at least 0.06 mg/mL, at least 0.07 mg/mL, at least 0.08 mg/mL, at least 0.09 mg/mL, or at least 0.1 mg/mL. In some implementations, a therapeutic composition includes a mean, average, or absolute amount of a cytokine or growth factor in a range of 0.01-0.1 mg/mL, 0.2-0.1 mg/mL, 0.03-0.01 mg/mL, or 0.04-0.1 mg/mL.

Nanoparticles

In some implementations, a therapeutic composition includes nanoparticles (e.g., a plurality of nanoparticles). In some implementations, a therapeutic composition includes or consists of blood derived nanoparticles (e.g., a plurality of nanoparticles). In some implementations, the nanoparticles include or consist of exosomes. In some implementations, the nanoparticles include or consist of endosomes. In some implementations, a nanoparticle or exosome includes a membrane-bound or membrane-encapsulated vesicle. In some implementations, a nanoparticle includes a membrane-bound or membrane-encapsulated vesicle where the membrane component includes a phospholipid bilayer. In some implementations, a nanoparticle is derived from blood. In some implementations, a nanoparticle is a synthetic membrane encapsulated vesicle that can be loaded with a membrane-bound or intra-vesicular cargo of choice. In some implementations, the nanoparticles are autologous to the subject and derived from the same subject's blood or plasma. In some implementations, the nanoparticles are heterologous to the subject. In some implementations, the therapeutic composition includes a mixture of heterologous nanoparticles and autologous nanoparticles to the subject.

Nanoparticles or exosomes derived from blood as described in this specification differ from exosomes derived from other sources. Blood-derived exosomes differ in their miRNA content, as well as their protein content from exosomes found in other bodily fluids, such as milk, blood, or urine.

In some implementations, nanoparticles as described in this specification have a mean, average, or absolute diameter of at least 10 nm, at least 25 nm, at least 40 nm, at least 50 nm, at least 55 nm, at least 60 nm, at least 70 nm, at least 80 nm, at least 90 nm or at least 100 nm. In some implementations, nanoparticles as described in this specification have a mean, average, or absolute diameter of at least 50 nm. In some implementations, nanoparticles as described in this specification have a mean, average, or absolute diameter in a range of about 10 nm to 300 nm, 30 nm to 300 nm, 40 nm to 300 nm, 50 nm to 300 nm, 50 nm to 250 nm, 50 nm to 250 nm, 50 nm to 200 nm, 75 nm to 200 nm, or 100 nm to 150 nm. In some implementations, nanoparticles as described in this specification have a mean, average, or absolute diameter in a range of about 100 to 200 nm. In some implementations, nanoparticles as described in this specification have a mean, average, or absolute diameter of about 100 nm, 125 nm, 150 nm, 175 nm or about 200 nm.

In some implementations, a nanoparticle as described in this specification includes one or more surface-bound proteins, non-limiting examples of which include CD41a, CD9, CD63 and CD81. In some implementations, a nanoparticle as described in this specification includes one or more, two or more, five or more, or ten or more surface-bound proteins selected from CD41a, CD9, CD63, CD81, CD326, CD133, CD14, CD24, CD42a, CD44, CD29, CD146, HLA-DR, HLA-DP and HLA-DQ. In some implementations, a nanoparticle as described in this specification includes three or more surface-bound proteins selected from the group consisting of CD41a, CD9, CD63 and CD81. In some implementations, a nanoparticle as described in this specification includes one or more or two or more surface-bound proteins selected from CD9, CD63 and CD81. In some implementations, a nanoparticle as described in this specification includes surface-bound CD41a.

In some implementations, a nanoparticle as described in this specification includes one or more microRNAs (miRNAs). In certain implementations, an miRNA is a small non-coding RNA molecule, sometimes containing about 22 nucleotides, that often functions in RNA silencing and post-transcriptional regulation of gene expression. In some implementations, a nanoparticles as described in this specification includes one or more miRNAs, non-limiting examples of which include hsa-miR-576-3p, hsa-miR-140-5p, hsa-miR-133a-3p, hsa-mir-206, hsa-miR-381-3p, hsa-mir-503, hsa-miR-374b-3p, hsa-mir-224, hsa-mir-18a, hsamir-363, hsa-mir-6513, hsa-mir-197, hsa-miR-6499-3p, hsa-mir-1246, hsa-miR-1306-5p, hsa-miR-23a-3p, hsa-mir-3180-5, hsa-miR-2110, hsa-miR-155, hsa-miR-483-3p, hsa-miR-146a-5p, hsa-mir-548a-2, hsa-miR-425-3p, hsa-let-7a-3p, hsa-miR-532-3p, hsa-miR-146a, hsa-mir-93, hsa-mir-6499, hsa-miR-101-5p, hsa-mir-20b, hsa-miR-6771-3p, hsa-miR-548bc, hsa-mir-6730, hsa-mir-181c, hsa-mir-10395, hsa-miR-496, hsa-mir-381, hsa-miR-320c, hsa-miR-3074-5p, hsa-mir-885, hsa-mir-377, hsa-mir-23a, hsa-miR-486-3p, hsa-mir-23b, hsa-miR-766-3p, hsa-miR-487b-3p, hsa-miR-330-3p, hsa-mir-101-1, hsa-miR-92b-5p, hsa-mir-7-3, hsa-miR-11400, hsa-miR-3124-5p, hsa-miR-191-3p, hsa-mir-4450, hsa-miR-3928-3p, hsa-miR-32-5p, hsa-miR-1301-3p, hsa-miR-370-3p, hsa-mir-151b, hsa-miR-574-3p, hsa-let-7b-5p, hsa-miR-30a-5p, hsa-mir-199a-1, hsa-miR-136-3p, hsa-miR-576-5p, hsa-mir-196a-2, hsa-mir-1-1, hsa-mir-370, hsa-miR-151b, hsa-mir-190a, hsa-mir-3173, hsa-miR-96-5p, hsa-mir-556, hsa-miR-106a-3p, hsa-mir-542, hsa-mir-130b, hsa-miR-641, hsa-miR-1285-3p, hsa-miR-30a-3p, hsa-mir-3960, hsa-miR-20b-5p, hsa-miR-1260a, hsa-mir-324, hsa-mir-299, hsa-mir-32, hsa-miR-891a-5p, hsa-mir-200a, hsa-miR-106b-5p, hsa-mir-6859-4, hsa-miR-379-5p, hsa-mir-648, hsa-miR-1255b-5p, hsa-let-7g-5p, hsa-mir-1199, hsa-mir-99a, hsa-miR-106a-5p, hsa-mir-182, hsa-mir-4634, hsa-mir-625, hsa-miR-6892-5p, hsa-miR-328-3p, hsa-mir-3194, hsa-mir-1255b-2, hsa-mir-126, hsa-miR-1908-5p, hsa-miR-2277-3p, hsa-miR-551b-3p, hsa-mir-7113, hsa-miR-3615, hsa-mir-342, hsa-miR-4508, hsa-mir-127, hsa-miR-4521, hsa-miR-33a-5p, hsa-miR-1287-5p, hsa-miR-154-5p, hsa-miR-1226-3p, hsa-miR-127-3p, hsa-miR-23b-3p, hsa-let-7a-2, hsa-let-7g, hsa-mir-3180-1, hsa-miR-98-3p, hsa-mir-190b, hsa-mir-221, hsa-miR-148b-5p, hsa-miR-1843, hsa-mir-26a-2, hsa-miR-3960, hsa-mir-6503, hsa-miR-31-5p, hsa-mir-548d-1, hsa-mir-1304, hsa-mir-4738, hsa-miR-126-5p, hsa-mir-3652, hsa-mir-10399, hsa-miR-139-3p, hsa-miR-376c-3p, hsa-miR-30b-5p, hsa-mir-431, hsa-miR-9-3p, hsa-mir-624, hsa-miR-551b, hsa-mir-641, hsa-miR-139-5p, hsa-miR-10401-3p, hsa-miR-941, hsa-miR-301a-5p, hsa-mir-128-1, hsa-miR-340-3p, hsa-miR-451a, hsa-miR-126-3p, hsa-mir-106b, hsa-mir-6803, hsa-mir-544a, hsa-miR-103a-3p, hsa-let-7i-3p, hsa-miR-199b-5p, hsa-miR-450a-1-3p, hsa-mir-497, hsa-miR-329-3p, hsa-mir-143, hsa-mir-9-1, hsa-miR-3188, hsa-miR-224-5p, hsa-mir-329-2, hsa-miR-92a-1, hsa-miR-548ax, hsa-mir-320a, hsa-mir-137, hsa-miR-144-3p, hsa-miR-499a-5p, hsa-miR-374a-3p, hsa-miR-141-3p, hsa-miR-339-5p, hsa-miR-186-5p, hsa-miR-486-5p, hsa-miR-548j-5p, hsa-miR-548ay-5p, hsa-miR-218-5p, hsa-miR-146b, hsa-mir-618, hsa-miR-4656, hsa-miR-135a-5p, hsa-mir-450b, hsa-mir-125a, hsa-miR-93-5p, hsa-miR-548k, hsa-miR-10395-5p, hsa-mir-196b, hsa-mir-185, hsa-mir-19b-1, hsa-miR-1304-3p, hsa-mir-1226, hsa-mir-1307, hsa-mir-320c-1, hsa-mir-29b-2, hsa-mir-148b, hsa-mir-30a, hsa-mir-941-1, hsa-mir-556-3p, hsa-miR-564, hsa-miR-5480-5p, hsa-mir-1538, hsa-miR-423-5p, hsa-miR-9901, hsa-miR-200a-3p, hsa-miR-548e-3p, hsa-mir-6724-2, hsa-mir-328, hsa-mir-1270, hsa-mir-320b-2, hsa-mir-376c, hsa-miR-155-5p, hsa-miR-6734-5p, hsa-mir-27a, hsa-let-7d-3p, hsa-mir-548o-2, hsa-mir-942, hsa-mir-362, hsa-miR-500a-3p, hsa-mir-3158-2, hsa-miR-22-3p, hsa-miR-411-5p, hsa-miR-505, hsa-mir-4665, hsa-mir-301a, hsa-mir-199b, hsa-mir-191, hsa-mir-3065, hsa-miR-502-3p, hsa-mir-193b, hsa-miR-500b-5p, hsa-mir-597, hsa-mir-20a, hsa-miR-542-3p, hsa-miR-589-5p, hsa-miR-181c-3p, hsa-mir-181a-2-3p, hsa-mir-590, hsa-miR-4732-3p, hsa-miR-335-3p, hsa-miR-125b-2, hsa-mir-139, hsa-mir-2355, hsa-miR-18b-5p, hsa-miR-18a-5p, hsa-mir-1843, hsa-mir-8072, hsa-mir-574, hsa-miR-7-1-3p, hsa-miR-374a-5p, hsa-miR-6513-3p, hsa-miR-135a-1, hsa-miR-28-3p, hsa-miR-10a-5p, hsa-miR-29b-2-5p, hsa-mir-7-2, hsa-miR-10396b-3p, hsa-miR-101-3p, hsa-miR-6134, hsa-mir-500b, hsa-mir-6125, hsa-miR-7-1, hsa-mir-222, hsa-miR-24-3p, hsa-miR-598-3p, hsa-miR-134-5p, hsa-mir-564, hsa-miR-182-3p, hsa-miR-625-3p, hsa-miR-6852-3p, hsa-mir-548a-1, hsa-mir-337, hsa-miR-3679-5p, hsa-mir-3180-4, hsa-miR-548c-5p, hsa-mir-215, hsa-miR-15b-3p, hsa-miR-7704, hsa-miR-196b-5p, hsa-miR-181b-5p, hsa-miR-409-5p, hsa-mir-152, hsa-miR-6850-5p, hsa-let-7e, hsa-mir-6859-3, hsa-mir-548e, hsa-miR-624-5p, hsa-miR-193b-5p, hsa-mir-17, hsa-mir-296, hsa-mir-28, hsa-miR-29b-3p, hsa-miR-4433b-5p, hsa-miR-6513-5p, hsa-mir-6850, hsa-miR-431-5p, hsa-miR-6516-3p, hsa-mir-5481, hsa-mir-486-1, hsa-miR-421, hsa-miR-543, hsa-miR-151a-5p, hsa-mir-1908, hsa-mir-6720, hsa-mir-4322, hsa-miR-148a-3p, hsa-mir-1-2, hsa-miR-570-3p, hsa-mir-103a-2, hsa-miR-324-3p, hsa-mir-339, hsa-mir-376a-2, hsa-mir-7704, hsa-mir-1277, hsa-mir-424, hsa-mir-1181, hsa-mir-329-1, hsa-mir-941-5, hsa-mir-1229, hsa-miR-484, hsa-mir-199a-2, hsa-mir-205, hsa-miR-6724-5p, hsa-mir-450a-1, hsa-mir-493, hsa-mir-130a, hsa-mir-10401, hsa-miR-320d, hsa-miR-95-3p, hsa-miR-4688, hsa-miR-222-3p, hsa-miR-378d-1, hsa-mir-11400, hsa-mir-29c, hsa-miR-1277-3p, hsa-miR-30e-3p, hsa-miR-382, hsa-miR-221-3p, hsa-miR-4999-5p, hsa-mir-30b, hsa-mir-181b-1, hsa-miR-652-3p, hsa-miR-651, hsa-miR-4662a-5p, hsa-mir-1271, hsa-mir-3688-1, hsa-miR-3158-3p, hsa-mir-4454, hsa-mir-323b, hsa-mir-5696, hsa-mir-181a-2, hsa-mir-203a, hsa-miR-3187-5p, hsa-mir-25, hsa-mir-219b, hsa-mir-369, hsa-mir-10396b, hsa-mir-3679, hsa-mir-25-5p, hsa-miR-137-3p, hsa-miR-3178, hsa-let-7i, hsa-mir-345, hsa-miR-99b-5p, hsa-mir-451a, hsa-mir-24-1, hsa-miR-548au-5p, hsa-miR-494-3p, hsa-miR-221-5p, hsa-let-7a-1, hsa-let-7b, hsa-let-7f-2-3p, hsa-miR-215-5p, hsa-miR-150-5p, hsa-miR-361-3p, hsa-miR-628-5p, hsa-let-7f-1, hsa-miR-345-5p, hsa-miR-877-5p, hsa-mir-889, hsa-mir-4754, hsa-mir-548d-2, hsa-mir-3190, hsa-miR-199a-3p, hsa-miR-30d-3p, hsa-miR-1307-5p, hsa-mir-941-2, hsa-miR-34a-5p, hsa-miR-335-5p, hsa-miR-26a-5p, hsa-miR-99b-3p, hsa-mir-34a, hsa-miR-190a-5p, hsa-mir-4479, hsa-mir-4497, hsa-mir-128-2, hsa-miR-3188, hsa-let-7a-5p, hsa-miR-7-5p, hsa-mir-192, hsa-mir-30c-1, hsa-mir-409, hsa-mir-410, hsa-miR-331-3p, hsa-mir-766, hsa-miR-4433b-3p, hsa-miR-382-5p, hsa-mir-133a-1, hsa-mir-654, hsa-miR-5010-3p, hsa-mir-100, hsa-mir-338, hsa-mir-361, hsa-miR-409-3p, hsa-miR-204-5p, hsa-mir-550a-1, hsa-miR-183-5p, hsa-mir-3200, hsa-miR-501-3p, hsa-mir-134, hsa-mir-1301, hsa-mir-378c, hsa-mir-144, hsa-miR-1197, hsa-miR-21-5p, hsa-miR-197-3p, hsa-mir-3605, hsa-miR-145-5p, hsa-mir-454, hsa-mir-218-1, hsa-mir-98, hsa-mir-92b, hsa-miR-4466, hsa-miR-496, hsa-mir-3178, hsa-mir-6734, hsa-miR-210-3p, hsa-miR-30d-5p, hsa-mir-22, hsa-miR-17-5p, hsa-miR-3200-5p, hsa-miR-92b-3p, hsa-mir-6084, hsa-miR-3187-3p, hsa-mir-103a-1, hsa-mir-4508, hsa-mir-421, hsa-mir-19a, hsa-miR-4732-5p, hsa-miR-193a-5p, hsa-mir-6771, hsa-mir-550a-3, hsa-mir-145, hsa-miR-500a-5p, hsa-miR-744-5p, hsa-miR-26a-2-3p, hsa-mir-6892, hsa-miR-3605-3p, hsa-mir-548ae-2, hsa-miR-378d, hsa-miR-205-5p, hsa-mir-1976, hsa-mir-4785, hsa-mir-10a, hsa-miR-3173-5p, hsa-miR-223-3p, hsa-miR-142-5p, hsa-miR-6803-3p, hsa-mir-655, hsa-mir-6724-3, hsa-miR-186-3p, hsa-mir-30c-2, hsa-miR-10a-3p, hsa-miR-1-3p, hsa-mir-5687, hsa-miR-146b-3p, hsa-mir-548au, hsa-miR-10399-3p, hsa-mir-150, hsa-mir-374a, hsa-mir-3187, hsa-miR-769-5p, hsa-miR-19a-3p, hsa-miR-1260b, hsa-miR-342-3p, hsa-miR-584-5p, hsa-mir-135a-2, hsa-mir-7977, hsa-miR-542-5p, hsa-miR-19b-3p, hsa-miR-199a-5p, hsa-mir-223, hsa-mir-320b-1, hsa-mir- 24-2, hsa-mir-193a, hsa-miR-548ad-5p, hsa-mir-1468, hsa-miR-339-3p, hsa-miR-1246, hsa-mir-501, hsa-miR-548ae-5p, hsa-mir-194-1, hsa-mir-485, hsa-mir-891a, hsa-mir-195, hsa-miR-200c-3p, hsa-mir-3124, hsa-miR-17-3p, hsa-mir-4645, hsa-mir-3180-3, hsa-miR-3200-3p, hsa-miR-320e, hsa-mir-1180, hsa-mir-200c, hsa-mir-4656, hsa-mir-4999, hsa-mir-545, hsa-mir-16-2, hsa-mir-598, hsa-miR-1307-3p, hsa-miR-376a-3p, hsa-miR-3065-5p, hsa-mir-30e, hsa-mir-125b-1, hsa-miR-125b-2-3p, hsa-miR-548am-5p, hsa-miR-323b-3p, hsa-mir-5091, hsa-miR-223-5p, hsa-miR-26b-5p, hsa-mir-7703, hsa-miR-628-3p, hsa-miR-532-5p, hsa-mir-4448, hsa-miR-378a-5p, hsa-mir-181b-2, hsa-mir-4521, hsa-miR-20a-5p, hsa-miR-21-3p, hsa-miR-6859-5p, hsa-mir-9-3, hsa-miR-2355-3p, hsa-miR-148b-3p, hsa-miR-590-3p, hsa-miR-100-5p, hsa-mir-374b, hsa-miR-320a-3p, hsa-mir-548bc, hsa-miR-301a-3p, hsa-mir-181a-1, hsa-mir-548k, hsa-miR-152-3p, hsa-miR-361-5p, hsa-mir-140, hsa-mir-550a-2, hsa-mir-379, hsa-mir-570, hsa-mir-548am, hsa-miR-23c, hsa-mir-425, hsa-mir-181d, hsa-mir-141, hsa-let-7i-5p, hsa-mir-331, hsa-mir-629, hsa-mir-320d-2, hsa-miR-654-3p, hsa-miR-429, hsa-miR-548d-5p, hsa-miR-324-5p, hsa-miR-26a-1-3p, hsa-mir-589, hsa-miR-1270, hsa-miR-3168, hsa-miR-143-3p, hsa-mir-365b, hsa-miR-10b-5p, hsa-miR-4454, hsa-miR-423-3p, hsa-miR-331-5p, hsa-miR-762, hsa-mir-941-3, hsa-miR-3181, hsa-miR-548e-5p, hsa-miR-651-5p, hsa-mir-6869, hsa-mir-326, hsa-miR-146b-5p, hsa-miR-378a-3p, hsa-miR-6730-5p, hsa-mir-548ay, hsa-miR-15b-5p, hsa-mir-3688-2, hsa-mir-33b, hsa-miR-10399-5p, hsa-miR-128-3p, hsa-mir-769, hsa-mir-133a-2, hsa-mir-4433b, hsa-mir-1972-1, hsa-miR-342-5p, hsa-miR-1229-3p, hsa-mir-15a, hsa-mir-1255b-1, hsa-mir-138-2, hsa-miR-145-3p, hsa-miR-29c-3p, hsa-let-7f-5p, hsa-miR-483-5p, hsa-mir-877, hsa-mir-3143, hsa-let-7d-5p, hsa-miR-30e-5p, hsa-miR-1271-5p, hsa-let-7c, hsa-miR-18a-3p, hsa-miR-369-5p, hsa-mir-378d-2, hsa-miR-4450, hsa-mir-6750, hsa-miR-9851-5p, hsa-mir-4688, hsa-miR-130b-5p, hsa-mir-1306, hsa-miR-144-5p, hsa-miR-122-5p, hsa-miR-206, hsa-mir-340, hsa-miR-136-5p, hsa-miR-8072, hsa-miR-340-5p, hsa-miR-485-3p, hsa-miR-25-3p, hsa-mir-664a, hsa-miR-3688-3p, hsa-let-7f-2, hsa-miR-425-5p, hsa-miR-181c-5p, hsa-miR-338-3p, hsa-mir-101-2, hsa-miR-140-3p, hsa-miR-625-5p, hsa-miR-486-2, hsa-mir-210, hsa-miR-369-3p, hsa-mir-1273h, hsa-miR-132-3p, hsa-mir-27b, hsa-miR-130a-3p, hsa-miR-142-3p, hsa-miR-4306, hsa-mir-744, hsa-mir-411, hsa-miR-27a-3p, hsa-miR-671-5p, hsa-mir-671, hsa-miR-33b-5p, hsa-mir-2110, hsa-mir-6724-4, hsa-mir-2277, hsa-miR-4306, hsa-mir-96, hsa-miR-185-5p, hsa-miR-26b, hsa-mir-3615, hsa-mir-455, hsa-mir-4710, hsa-let-7d, hsa-mir-660, hsa-mir-762, hsa-miR-9-5p, hsa-mir-99b, hsa-mir-6852, hsa-miR-378c, hsa-miR-125a-5p, hsa-mir-548ax, hsa-miR-493-3p, hsa-miR-99a-5p, hsa-mir-151a, hsa-miR-497-5p, hsa-mir-502, hsa-miR-363-3p, hsa-mir-1185-1, hsa-mir-429, hsa-mir-3976, hsa-miR-6869-5p, hsa-miR-493-5p, hsa-mir-3928, hsa-miR-629-5p, hsa-mir-21, hsa-miR-181d-5p, hsa-mir-10b, hsa-miR-22-5p, hsa-miR-28-5p, hsa-miR-320c-2, hsa-miR-323a-3p, hsa-mir-584, hsa-mir-204, hsa-mir-92a-2, hsa-miR-182-5p, hsa-mir-3143, hsa-miR-132-5p, hsa-mir-122, hsa-let-7a-3, hsa-mir-548at, hsa-miR-30c-5p, hsa-miR-455-5p, hsa-miR-23c, hsa-mir-12136, hsa-mir-330, hsa-mir-16-1, hsa-miR-299-5p, hsa-mir-7977, hsa-mir-183, hsa-miR-10b-3p, hsa-miR-454-5p, hsa-mir-107, hsa-mir-9851, hsa-miR-92a-3p, hsa-mir-7976, hsa-mir-1285-1, hsa-miR-660-5p, hsa-mir-4732, hsa-mir-3909, hsa-miR-12136, hsa-miR-151a-3p, hsa-miR-26b-5p, hsa-miR-1468-5p, hsa-mir-6842, hsa-mir-1256, hsa-mir-323a, hsa-miR-106b-3p, hsa-miR-942-5p, hsa-mir-3074, hsa-miR-98-5p, hsa-miR-29a-3p, hsa-miR-362-5p, hsa-mir-18b, hsa-miR-505-3p, hsa-miR-15a-5p, hsa-miR-550a-3-5p, hsa-mir-194-2, hsa-miR-432-5p, hsa-mir-484, hsa-mir-3180-2, hsa-mir-4290, hsa-miR-4290, hsa-mir-6859-1, hsa-mir-320e, hsa-miR-1180-3p, hsa-miR-548at-5p, hsa-miR-664a-3p, hsa-miR-143-5p, hsa-mir-483, hsa-mir-432, hsa-miR-503-5p, hsa-mir-335, hsa-mir-30d, hsa-miR-1260b, hsa-miR-185-3p, hsa-mir-941-4, hsa-mir-31, hsa-mir-33a, hsa-miR-374b-5p, hsa-miR-29c-5p, hsa-miR-23b-5p, hsa-miR-125b-5p, hsa-mir-29a, hsa-mir-576, hsa-mir-652, hsa-mir-1260a, hsa-mir-4772, hsa-mir-638, hsa-miR-671-3p, hsa-miR-545-3p, hsa-mir-548c, hsa-mir-132, hsa-miR-184, hsa-mir-1185-2, hsa-miR-93-3p, hsa-miR-195-5p, hsa-mir-548j, hsa-miR-125a-3p, hsa-mir-1203, hsa-mir-6516, hsa-miR-450b-5p, hsa-mir-3168, hsa-mir-7706, hsa-mir-19b-2, hsa-miR-4662a, hsa-mir-3158-1, hsa-mir-142, hsa-miR-424-5p, hsa-miR-194-5p, hsa-miR-6842-3p, hsa-mir-494, hsa-miR-190b-5p, hsa-miR-548a-3p, hsa-miR-7976, hsa-mir-136, hsa-mir-628, hsa-mir-184, hsa-miR-597-5p, hsa-miR-550a-3p, hsa-mir-154, hsa-let-7e-5p, hsa-mir-3181, hsa-mir-487b, hsa-mir-9901, hsa-mir-548ad, hsa-mir-26a-1, hsa-mir-376a-1, hsa-mir-423, hsa-mir-1197, hsa-mir-5010, hsa-miR-181a-3p, hsa-miR-664a-5p, hsa-miR-16-2-3p, hsa-miR-181a-5p, hsa-mir-500a, hsa-mir-4685, hsa-miR-320b, hsa-mir-186, hsa-mir-664b, hsa-miR-192-5p, hsa-miR-320d-1, hsa-miR-5481, hsa-mir-1287, hsa-miR-130b-3p, hsa-let-7c-5p, hsa-miR-203a-3p, hsa-miR-377-3p, hsa-miR-199b-3p, hsa-miR-454-3p, hsa-mir-106a, hsa-mir-148a, hsa-miR-107, hsa-miR-378a, hsa-miR-15b, hsa-miR-889-3p, hsa-miR-548a-3, hsa-mir-4449, hsa-mir-95, hsa-mir-532, hsa-mir-29b-1, hsa-miR-27b-3p, hsa-miR-326, hsa-mir-6724-1, hsa-miR-1185-1-3p, hsa-miR-16-5p, hsa-miR-9-2, hsa-miR-4785, hsa-mir-499a, hsa-miR-7706, hsa-miR-1976, and hsa-miR-191-5p.

In some implementations, a nanoparticle as described in this specification includes one or more soluble proteins, non-limiting examples of which include enzymes, hormones, cytokines and growth factors. In some implementations, a nanoparticle as described in this specification includes one or more soluble proteins commonly detected in plasma, non-limiting examples of which include enzymes, hormones, cytokines and growth factors. In some implementations, a nanoparticle includes one or more soluble proteins detected in human plasma. In some implementations, a nanoparticle as described in this specification includes one or more soluble proteins detected in human plasma, non-limiting examples of which include adhesive proteins such as Von Willebrand factor, fibrinogen, trombospondi-1, trombospondin-2, and laminin-8); growth factors such as Epidermal growth factor (EGF), insulin-like growth factor 1 (IGF-1), hepatocyte growth factor (HGF), and transforming growth factor β (TGF-β); angiogenic factors such as Vascular endothelium growth factor (VEGF), platelet-derived growth factor (PDGF), and fibroblast growth factor (FGF); chemokines such as CCL5 (RANTES), CCL-3 (MIP-1a), CCL-2 (MCP-1), CCL-7 (MCP-3), CXCL8 (IL-8), CXCL2 (MIP-2), CXCL6 (LIX), CXCL-1 (GRO-a), CXCL5 (ENA-78), CXCL-12 (SDF-1a), and CXCL4 (PF4); clotting factors and their inhibitors such as Factor V, factor IX, antithrombin, factor S, protease nexin-1, protease nexin-2, and tissue factor pathway inhibitor; integral membrane proteins such as aIIb3, GPIba-IX-V, GPVI, TLT-1, and p-selectin; and immune mediators such as Complement C3 precursor, complement C4 precursor, factor D, factor H, C1 inhibitor, and IgG.

Methods

Described in this specification are technologies including compositions and methods for treating a disease or disorder, or inhibiting, reducing the severity of, or ameliorating one or more symptoms or secondary complications of a disease or disorder described herein, where a method includes administering a composition described herein to a subject in need thereof. In some implementations, a method of treating a disease or disorder in a subject in need thereof, includes administering to the subject a therapeutically effective amount of the therapeutic composition or pharmaceutical composition described herein.

In some implementations, a method includes treating arthritis, or chronic or acute inflammation of the joints. In some implementations, a method includes inhibiting, reducing the severity of, or ameliorating one or more symptoms of arthritis, or chronic or acute inflammation of the joints. In some implementations, an arthritis is osteoarthritis or rheumatoid arthritis.

Subjects

The term "subject" refers to a mammal. Any suitable mammal can be treated by a method or composition described herein. Non-limiting examples of mammals include a human, non-human primate (e.g., ape, gibbons, chimpanzees, orangutans, monkeys, macaques, and the like), domestic animals (e.g., dogs and cats), farm animals (e.g., horses, cows, goats, sheep, pigs) or experimental animals (e.g., mouse, rat, rabbit, guinea pig). In some implementations a subject is a non-human primate or a human. In some implementations a subject is a human. A subject can be any age or at any stage of development (e.g., an adult, teen, child, infant, or a mammal in utero). A subject can be male or female.

In some implementations, a subject is suffering from arthritis. In some implementations, the arthritis is osteoarthritis or rheumatoid arthritis. In some implementations, the arthritis is osteoarthritis. In some implementations, the arthritis is rheumatoid arthritis.

In some implementations, the subject suffers from joint pain. In some implementations, the joint pain is derived from arthritis. In some implementations, the arthritis is osteoarthritis or rheumatoid arthritis. In some implementations, the subject suffers from hand pain, shoulder pain, hip pain and/or knee pain. In some implementations, the joint pain affects the subject's hand, wrist, elbow, shoulder, hip, knee, ankle, feet, cervical spine, lumbar spine, thoracic spine, sacrum, and/or coccyx. In some implementations, the joint pain affects a subject's hand. In some implementations, the joint pain affects a subject's wrist. In some implementations, the joint pain affects a subject's elbow. In some implementations, the joint pain affects a subject's shoulder. In some implementations, the joint pain affects a subject's hip. In some implementations, the joint pain affects a subject's knee. In some implementations, the joint pain affects a subject's ankle. In some implementations, the joint pain affects a subject's feet. In some implementations, the joint pain affects a subject's cervical spine. In some implementations, the joint pain affects a subject's lumbar spine. In some implementations, the joint pain affects a subject's thoracic spine. In some implementations, the joint pain affects a subject's sacrum. In some implementations, the joint pain affects a subject's coccyx.

In some implementations, a pharmaceutical composition as described in this specification includes a therapeutically effective amount of a therapeutic composition. In some implementations a pharmaceutical composition includes a therapeutic composition as described in this specification for use in treating a disease or disorder in a subject, or one or more symptoms thereof. In some implementations, a pharmaceutical composition includes a therapeutic composition as described in this specification and a pharmaceutically acceptable excipient, diluent, additive or carrier.

A pharmaceutical composition can be formulated for a suitable route of administration. In some implementations, a pharmaceutical composition is formulated for oral, subcutaneous (s.c.), intradermal, intramuscular, intratracheal, intraarticular, intraperitoneal and/or intravenous (i.v.) administration. In certain implementations, a pharmaceutical composition contains formulation materials for modifying, maintaining, or preserving, for example, the pH, osmolarity, viscosity, clarity, color, isotonicity, odor, sterility, stability, rate of dissolution or release, adsorption, or penetration of the composition. In certain implementations, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients; and/or pharmaceutical adjuvants. In particular, a pharmaceutical composition can include any suitable carrier, formulation, or ingredient, the like or combinations thereof such as those listed in "Remington: The Science And Practice Of Pharmacy" Mack Publishing Co., Easton, PA, $19^{th}$ Edition, (1995)(hereafter, Remington '95), or "Remington: The Science And Practice Of Pharmacy", Pharmaceutical Press, Easton, PA, $22^{nd}$ Edition, (2013)(hereafter, Remington 2013), the contents of which are incorporated by reference in their entirety.

In certain implementations, a pharmaceutical composition includes a suitable excipient, non-limiting examples of which include anti-adherents (e.g., magnesium stearate), a binder, fillers, monosaccharides, disaccharides, other carbohydrates (e.g., glucose, mannose or dextrin), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington '95 or Remington 2013. The term "binder" as used herein refers to a compound or ingredient that helps keep a pharmaceutical mixture combined. Suitable binders for making pharmaceutical formulations are often used in the preparation of pharmaceutical tablets, capsules and granules.

In some implementations a pharmaceutical composition includes a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agent include those having a sulfhydryl group (e.g., a thiol) such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutylhydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may include other commonly used ingredients, for example, inorganic salts such as sodium chloride, potassium chloride, calcium chloride, sodium phosphate, potassium phosphate, or sodium bicarbonate, as well as organic salts such as sodium citrate, potassium citrate, or sodium acetate.

The pharmaceutical compositions described in this specification can be stable over an extended period of time, for example, on the order of months or years. In some implementations, a pharmaceutical composition includes one or more suitable preservatives. Non-limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can include a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can include an alkyl-mercury salt of thiosalicylic acid, such as thimerosal, phenylmercuric nitrate, phenylmercuric acetate or phenylmercuric borate. A preservative can include a paraben, such as methylparaben or propylparaben. A preservative can include an alcohol, such as chlorobutanol, benzyl alcohol or phenyl ethyl alcohol. A preservative can include a biguanide derivative, such as chlorohexidine or polyhexamethylene biguanide. A preservative can include sodium perborate, imidazolidinyl urea, and/or sorbic acid. A preservative can include stabilized oxychloro complexes, such as known and commercially available under the trade name PURITE®. A preservative can include polyglycol-polyamine condensation resins, such as known and commercially available under the trade name POLYQUART® from Henkel KGaA. A preservative can include stabilized hydrogen peroxide. A preservative can be benzalkonium chloride. In some implementations, a pharmaceutical composition is free of preservatives.

In some implementations, a therapeutic composition or pharmaceutical composition as described herein is substantially free of contaminants (e.g., cells, blood cells, platelets, polypeptides, minerals, blood-borne compounds or chemicals, virus, bacteria, fungus, yeast, pathogens, toxins, parasites and the like).

In some implementations, a therapeutic composition or pharmaceutical composition described herein is substantially free of endotoxin. In some implementations a therapeutic composition or pharmaceutical composition described herein includes less than 5 EU/ml, less than 2.5 EU/ml, less than 1 EU/ml, less than 0.5 EU/ml, less than 0.1 EU/ml, or less than 0.05 EU/ml of endotoxin. In some implementations, a therapeutic composition or pharmaceutical composition described herein is sterile or aseptic.

The pharmaceutical compositions described in this specification may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some implementations, a pharmaceutical composition suitable for parenteral administration may contain one or more excipients. In some implementations a pharmaceutical composition is lyophilized to a dry powder form. In some implementations a pharmaceutical composition is lyophilized to a dry powder form, which is suitable for reconstitution with a suitable pharmaceutical solvent (e.g., water, saline, an isotonic buffer solution (e.g., PBS), DMSO, combinations thereof and the like). In certain implementations, reconstituted forms of a lyophilized pharmaceutical composition are suitable for parenteral administration (e.g., intravenous administration) to a mammal.

In certain implementations, a pharmaceutical composition is configured for oral administration and may be formulated as a tablet, microtablet, minitablets, micropellets, powder, granules, capsules (e.g., capsules filled with microtablets, micropellets, powders or granules), emulsions, solutions, the like or combinations thereof. Pharmaceutical compositions configured for oral administration may include suitable coatings to delay or sustain release of the active ingredient, non-limiting examples of which include enteric coatings such as fatty acids, waxes, shellac, plastics, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, cellulose acetate trimellitate, sodium alginate, zein, plant fibers, the like, and/or combinations thereof.

In some implementations, a pharmaceutical composition described herein may be configured for topical administration and may include one or more of a binding and/or lubricating agent, polymeric glycols, gelatins, cocoa-butter or other suitable waxes or fats. In some implementations, a pharmaceutical composition described as described in this specification is incorporated into a topical formulation containing a topical carrier that is generally suited to topical drug administration and comprising any suitable material known to those skilled in the art. In certain implementations, a topical formulation of a pharmaceutical composition is formulated for administration of a therapeutic composition described herein from a topical patch.

In certain implementations, an optimal pharmaceutical composition is determined by one skilled in the art depending upon, for example, the intended route of administration, delivery format and desired dosage (see e.g., Remington '95 or Remington 2013, supra). A pharmaceutical composition can be manufactured by any suitable manner, including, e.g., by means of conventional mixing, dissolving, granulating, dragee-making, levigating, emulsifying, encapsulating, entrapping or tableting processes (e.g., see methods described in Remington '95 or Remington 2013).

Route of Administration

Any suitable method of administering a therapeutic composition or pharmaceutical composition as described in this specification to a subject can be used. Any suitable formulation and/or route of administration can be used for administration of a therapeutic composition or pharmaceutical composition as described in this specification (e.g., see Fingl et al. 1975, in "The Pharmacological Basis of Therapeutics", which is incorporated herein by reference in its entirety). A suitable formulation and/or route of administration can be chosen by a medical professional (e.g., a physician) in view of, for example, a subject's disorder, disease, risk, age, and/or health condition. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like and combinations thereof. In some implementations, the therapeutic composition or pharmaceutical composition is administered intravenously or directly at the site of joint pain. In some implementations, the joint pain is hand pain, wrist pain, elbow pain, shoulder pain, hip pain, knee pain, ankle pain, feet pain, cervical spine pain, lumbar spine pain, thoracic spine pain, sacrum pain, and/or coccyx pain. In some implementations, the joint pain is hand pain. In some implementations, the joint pain is wrist pain. In some implementations, the joint pain is elbow pain. In some implementations, the joint pain is shoulder pain. In some implementations, the joint pain is hip pain. In some implementations, the joint pain is knee pain. In some implementations, the joint pain is ankle pain. In some implementations, the joint pain is feet pain. In some implementations, the joint pain is cervical spine pain. In some implementations, the joint pain is lumbar spine pain. In some implementations, the joint pain is thoracic spine pain. In some implementations, the joint pain is sacrum pain. In some implementations, the joint pain is coccyx pain. In some implementations, the therapeutic composition or pharmaceutical composition is administered by intravenous administration. In some implementations, the therapeutic composition or pharmaceutical composition is administered by intraarticular administration. In some implementations, the therapeutic composition or pharmaceutical composition is administered by periarticular administration. In some implementations, the therapeutic composition or pharmaceutical composition is administered by intraarticular administration. In some implementations, the therapeutic composition or pharmaceutical composition is administered by periarticular administration. In some implementations, the therapeutic composition or pharmaceutical composition is administered by subcutaneous administration. In some implementations, the therapeutic composition or pharmaceutical composition is administered by intradermal administration. In some implementations, the therapeutic composition or pharmaceutical composition is administered by intramuscular administration. In some implementations, the therapeutic composition or pharmaceutical composition is administered by one or more routes of administration, non-limiting examples of which include intravenous administration, intraarticular administration, periarticular administration, subcutaneous administration, intradermal administration, and intramuscular administration.

In some implementations a therapeutic composition or a pharmaceutical composition disclosed herein is provided to a subject. For example, a composition that is provided to a subject is sometimes provided to a subject for self-administration or for administration to a subject by another (e.g., a non-medical professional). As another example, a composition can be provided as an instruction written by a medical practitioner that authorizes a patient to be provided a composition or treatment described herein (e.g., a prescription). In yet another example, a composition can be provided to a subject where the subject self-administers a composition orally, intravenously or by way of an inhaler, for example.

Alternately, one can administer a composition as described in this specification in a local rather than systemic manner, for example, via direct application to the skin, mucous membrane or region of interest for treating, including using a depot or sustained release formulation.

In certain implementations a pharmaceutical composition comprising a composition described herein is administered alone (e.g., as a single active ingredient (AI or e.g., as a single active pharmaceutical ingredient (API)). In other implementations, a pharmaceutical composition comprising a therapeutic composition described herein is administered in combination with one or more additional AIs/APIs, for example, as two separate compositions or as a single composition where the one or more additional AIs/APIs are mixed or formulated together with a therapeutic or pharmaceutical composition described herein.

Dose and Therapeutically Effective Amount

In some implementations, an amount of a therapeutic or pharmaceutical composition as described in this specification is a therapeutically effective amount. In some implementations, a therapeutically effective amount of a therapeutic or pharmaceutical composition as described in this specification is an amount needed to obtain an effective therapeutic outcome, such as to treat, reduce the severity of, and/or inhibit, reduce or alleviate one or more symptoms of arthritis (e.g., osteoarthritis or rheumatoid arthritis). Determination of a therapeutically effective amount is well within the capability of those skilled in the art, especially in light of the detailed disclosure provided herein.

In certain implementations, a therapeutically effective amount is an amount high enough to provide an effective therapeutic effect (e.g., a beneficial therapeutic effect), but low enough to minimize unwanted adverse reactions. Accordingly, in certain implementations, a therapeutically effective amount of a therapeutic composition described herein may vary from subject to subject, often depending on age, weight, general health condition of a subject, severity of a condition being treated, and/or a particular combination of drugs administered to a subject. Thus, in some implementations, a therapeutically effective amount is determined empirically. Accordingly, a therapeutically effective amount of a therapeutic composition described herein that is administered to a subject can be determined by one of ordinary skill in the art based on amounts found effective in animal or clinical studies, a physician's experience, and suggested dose ranges or dosing guidelines, for example.

In certain implementations, a therapeutically effective amount of a composition as described in this specification (e.g., a therapeutic or pharmaceutical composition) is administered at a suitable dose (e.g., at a suitable volume, frequency and/or concentration, which often depends on a subject's weight, age and/or condition) intended to obtain an acceptable therapeutic outcome. In certain implementations, a therapeutically effective amount of a therapeutic composition as described in this specification includes one or more doses selected from at least 0.001 mg/kg (e.g., mg of total protein of a composition described herein per kg body weight of a subject), at least 0.01 mg/kg, at least 0.1 mg/kg, at least 1 mg/kg, at least 10 mg/kg or at least 100 mg/kg. In certain implementations, a therapeutically effective amount of a composition as described in this specification is selected from one or more doses of about 0.001 mg/kg (e.g., mg of a therapeutic composition described herein per kg body weight of a subject) to about 5000 mg/kg, 0.01 mg/kg to 1000 mg/kg, 0.01 mg/kg to 500 mg/kg, 0.1 mg/kg to 1000 mg/kg, 1 mg/kg to 1000 mg/kg, 10 mg/kg to 1000 mg/kg, 100 mg/kg to 1000 mg/kg, 0.1 mg/kg to 500 mg/kg, 0.1 mg/kg to 250 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg, and 0.5 mg/kg to 5 mg/kg, intervening amounts and combinations thereof. In some aspects a therapeutically effective amount of a composition as described in this specification that is administered to a subject includes one or more doses of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 50 mg/kg, 100 mg/kg, 500 mg/kg, and intervening amounts and combinations thereof. In some implementations a therapeutically effective amount of a therapeutic composition as described in this specification is between about 0.1 mg/kg and about 50 mg/kg.

In certain implementations, the amount of nanoparticles in a therapeutic or pharmaceutical composition is determined. Accordingly, in some implementations, a therapeutically effective amount of a composition as described in this specification (e.g., a therapeutic or pharmaceutical composition) is administered as a suitable dose of nanoparticles intended to obtain an acceptable therapeutic outcome. In certain implementations, a therapeutically effective amount of a composition as described in this specification includes one or more doses selected from at least $1.1 \times 10^8$ particles/kg (e.g., per kg body weight of a subject), at least $1.1 \times 10^9$ particles/kg, at least $1.1 \times 10^{10}$ particles/kg, at least $1.1 \times 10^{11}$ particles/kg, at least $1.1 \times 10^{12}$ particles/kg or at least $1.1 \times 10^{13}$ particles/kg. In certain implementations, a therapeutically effective amount of a composition as described in this specification is selected from one or more doses in a range of about $1.1 \times 10^8$ particles/kg (e.g., per kg body weight of a subject) to about $1.1 \times 10^{18}$ particles/kg, $1.1 \times 10^8$ particles/kg to $1.1 \times 10^{16}$ particles/kg, $1.1 \times 10^8$ particles/kg to $1.1 \times 10^{12}$ particles/kg, $1.0 \times 10^8$ particles/kg to $1.0 \times 10^{13}$ particles/kg, or $1.0 \times 10^{10}$ particles/kg to $1.0 \times 10^{13}$ particles/kg, intervening amounts and/or combinations thereof.

In some implementations, administering a therapeutically effective amount of a composition as described in this specification includes administering a suitable dose at a frequency or interval as needed to obtain an effective therapeutic outcome. In some implementations administering a therapeutically effective amount of a composition as described in this specification includes administering a suitable dose hourly, every two hours, every 4 hours, every 6 hours, three times a day, twice a day, once a day, six times a week, five times a week, four times a week, three times a week, twice a week, weekly, monthly, quarterly, biannually, annually at combinations thereof, and/or at regular or irregular intervals thereof, and/or simply at a frequency or interval as needed or recommended by a medical professional. In some implementations, a therapeutically effective amount of a composition as described in this specification is administered continuously, for example, by intravenous administration.

EXAMPLES

Example 1a—Method of Manufacturing

Organicell Patient Pure X (PPX) is an autologous biologic derived from peripheral whole blood. Whole blood is collected from a patient with ACD-A anticoagulant and shipped (24-48 hours) to Organicell in a blood transport container. Upon receipt, the whole blood is centrifuged at 2,000×g to precipitate the cellular component and separate the blood plasma. Plasma is collected and centrifuged at 100,000×g for 90-120 minutes to precipitate the nanoparticle fraction. The supernatant is removed, and the nanoparticle fraction is resuspended in sterile saline. The resuspended nanoparticle mixture is then filtered with a 0.22 uM filter and collected into a vial for use. The final PPX product can then be administered intra-venously or intra-articular to the patient in an autologous manner.

In an example implementation, whole blood is collected from a patient with ACD-A anticoagulant and shipped (24-48 hours) to Organicell in a blood transport container. Upon receipt, 50 ml of whole blood is centrifuged at 2,000×g for 10 minutes at a temperature of 20° C. to precipitate the cellular component and separate the blood plasma. In some implementations (optionally), the plasma is centrifuged again at 2,000×g for 5 minutes. After the centrifugation (one or both centrifugation runs), 12 ml of plasma is collected distributed to two 6 ml tubes. The tubes are centrifuged at 100,000×g for 90 minutes at a temperature of 4° C. to precipitate the nanoparticle fraction. The supernatant is removed, and the nanoparticle fraction (pellet) is resuspended in sterile saline (2 ml of saline in each tube). The resuspended nanoparticle mixture is then filtered with a 0.22 uM filter and collected into a vial for use. The final PPX product can then be administered intra-venously or intra-articular to the patient in an autologous manner.

Example 1b—Method of Manufacturing

An example product that can be used in the same way and for the same purpose as PPX is a heterologous biologic derived from peripheral whole blood. Whole blood is collected with ACD-A anticoagulant and shipped (24-48 hours) to Organicell in a blood transport container. Upon receipt, the whole blood is centrifuged at 2,000×g to precipitate the cellular component and separate the blood plasma. Plasma is collected and centrifuged at 100,000×g for 90-120 minutes to precipitate the nanoparticle fraction. The supernatant is removed, and the nanoparticle fraction is resuspended in sterile saline. The resuspended nanoparticle mixture is then filtered with a 0.22 uM filter and collected into a vial for use. The final product can then be administered intra-venously or intra-articular to a patient in a heterologous manner.

In an example implementation, whole blood is collected with ACD-A anticoagulant and shipped (24-48 hours) to Organicell in a blood transport container. Upon receipt, 50 ml of whole blood is centrifuged at 2,000×g for 10 minutes at a temperature of 20° C. to precipitate the cellular component and separate the blood plasma. In some implementations (optionally), the plasma is centrifuged again at 2,000×g for 5 minutes. After the centrifugation (one or both centrifugation runs), 12 ml of plasma is collected distributed to two 6 ml tubes. The tubes are centrifuged at 100,000×g for 90 minutes at a temperature of 4° C. to precipitate the nanoparticle fraction. The supernatant is removed, and the nanoparticle fraction (pellet) is resuspended in sterile saline (2 ml of saline in each tube). The resuspended nanoparticle mixture is then filtered with a 0.22 uM filter and collected into a vial for use. The final PPX product can then be administered intra-venously or intra-articular to a patient in a heterologous manner.

Example 2—Results

Figure 1B:
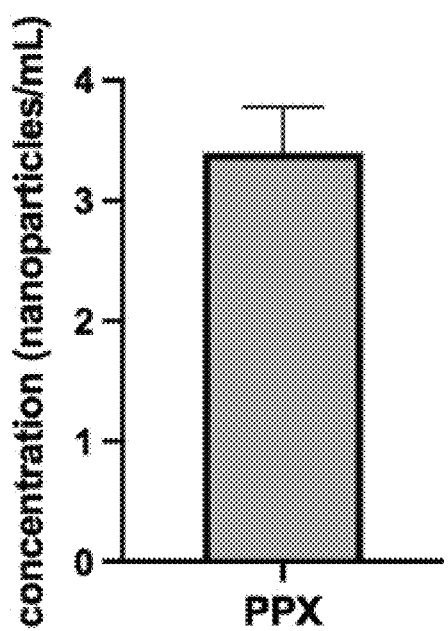
Figure 1C:
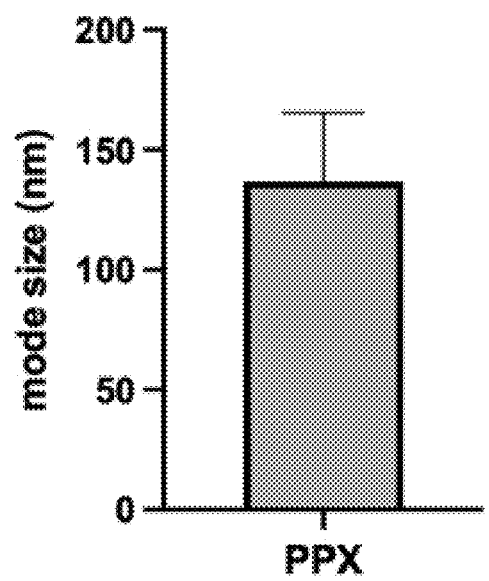
Figure 2A:
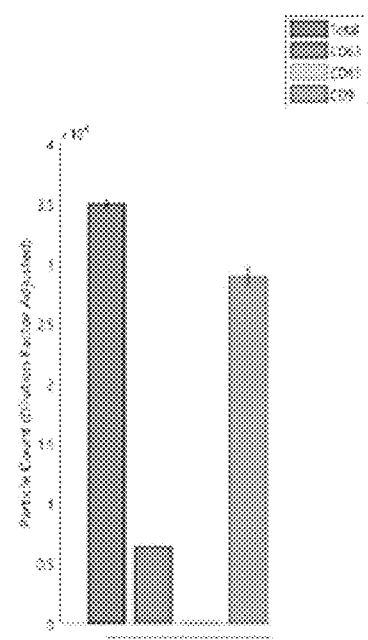
FIGS. 2A-2C present exemplary results of ExoView® analysis of PPX.
Figure 2B:
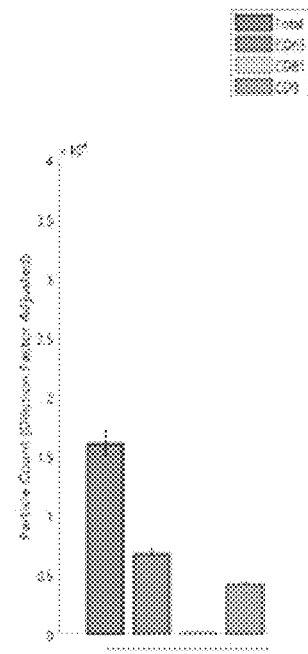
Figure 2C:
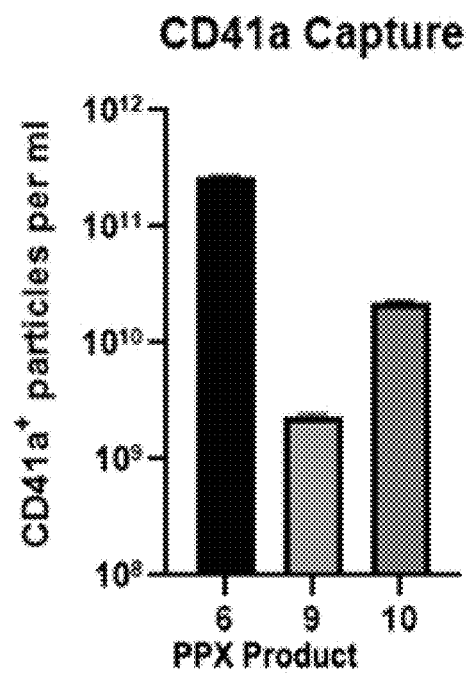
Figure 3:
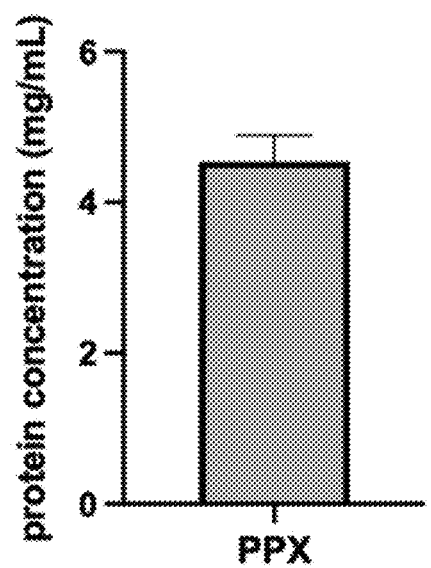
FIG. 3 is a bar graph showing protein concentration of PPX. Error bars represent the standard error of the mean.

An example PPX product contained soluble proteins as well as nanoparticles such as extracellular vesicles, lipoproteins, exosomes, and other cell derived components. Nanoparticle tracking analysis was performed to quantify and demonstrate the size distribution of the nanoparticle composition (FIG. 1A). The average nanoparticle concentration of PPX was $3.0 \times 10^{11}$ with a range of $5.0 \times 10^{10}$ to $5.0 \times 10^{11}$ (FIG. 1B). The average mode size of PPX was 130 nm with a range of 50 nm to 200 nm (FIG. 1C). Fluorescent nanoparticle imaging has been completed to identify the extracellular vesicle population in PPX. Using single particle interferometric reflectance imaging sensing (ExoView® R100, Nanoview Biosciences) analysis of the PPX nanoparticle population found various populations of extracellular vesicles. In this analysis, antibody coated chips (CD41a and CD63) captured CD41a+ and CD63+ nanoparticles and fluorescent conjugates binding to CD63, CD81, and CD9 were combined. Unbound antibodies were washed away and chips were visualized for fluorescent imaging to quantify the various populations of EVs co-expressing the various surface markers CD41a, CD63, CD81, and CD9 (FIGS. 2A and 2B). Moreover, comparison of the number of capture particles on the CD41a plate versus the CD63 plate showed a higher capture number of CD41a+ extracellular vesicles (FIGS. 2A and 2B). CD41a is a platelet marker, and it was demonstrated that PPX largely contained platelet derived extracellular vesicles. Approximation of CD41a EVs per mL could be achieved with this system [3]. The number of CD41a+ EVs in PPX was approximately $10^9$-$10^{12}$ EVs per mL (FIG. 2C). Moreover, the quantification of Bradford analysis of the PPX product demonstrated an average protein concentration of 4.5 mg/mL with a range of 2 to 10 mg/mL (FIG. 3).

Figure 4A:
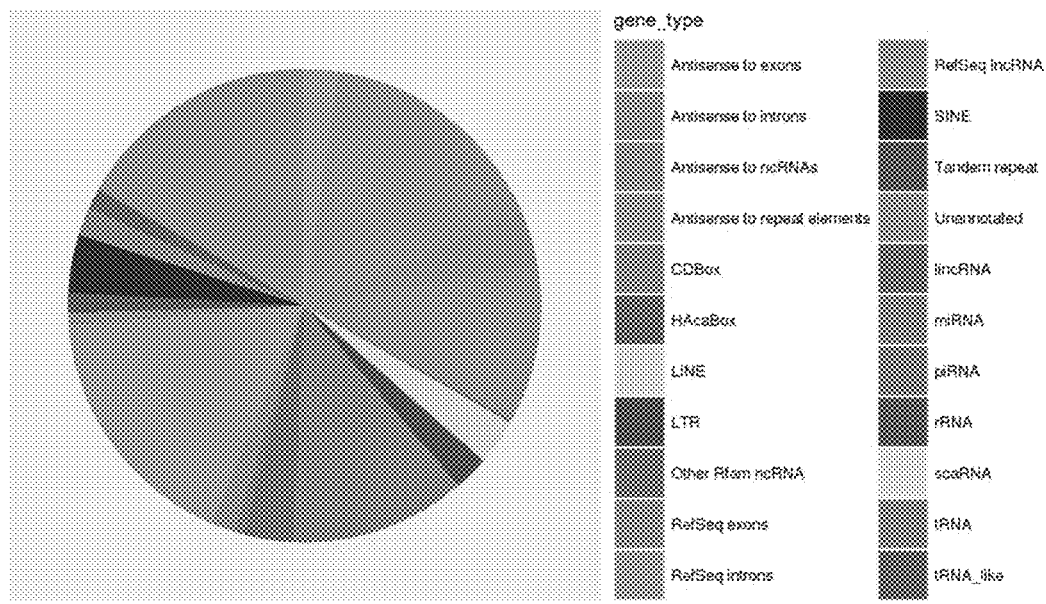
FIGS. 4A-4B present an exemplary small RNA sequencing of PPX nanoparticle cargo.
Figure 4B:
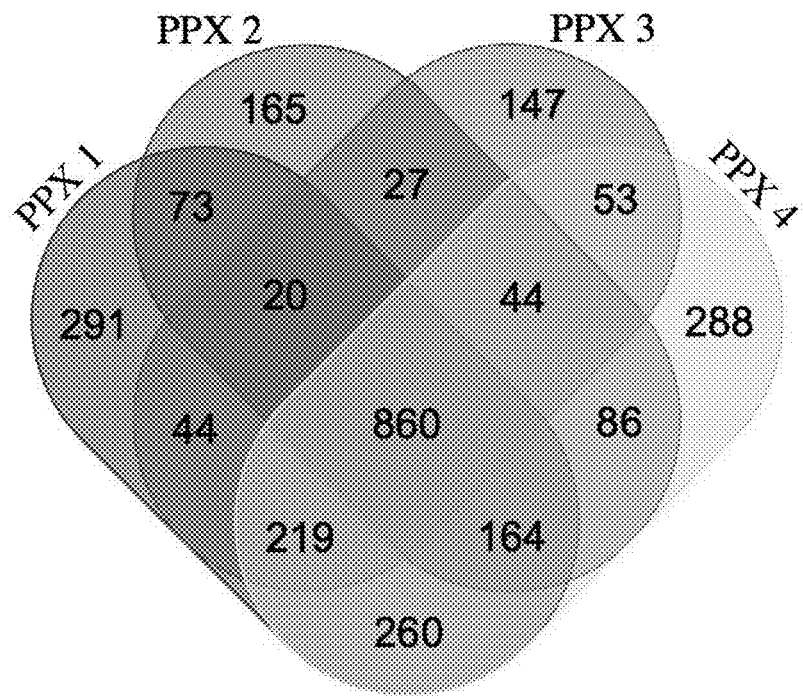

FIGS. 4A-4B show the results of an exemplary small RNA sequencing of PPX nanoparticle cargo. FIG. 4A is a circle chart showing an exemplary representative distribution of various RNA subtypes in an example PPX sample. FIG. 4B is a Venn diagram showing an exemplary comparative analysis of representative four PPX products (PPX1-4). The results from this study indicate that at least about 860 miRNAs can be reproducibly detected.

Example 3—Therapeutic Use of PPX

PPX can be administered intravenously or directly at the site of joint pain. Hand pain derived from osteoarthritis and rheumatoid arthritis can be similarly treated. Other joints such as hip, shoulder, and knees can be treated for similar sources of pain.

In an example implementation, a pilot clinical trial was conducted. The was approved by the Institute of Regenerative and Cellular Medicine (IRCM-2022-317). This clinical trial was designed as an open-label, 2 arm study using intravenous (IV) route of admiration vs intra-articular (IA) administration of a PPX formulation as described above. Subjects were diagnosed with osteoarthritis of the knee and were required to have a Kellgren-Lawrence Scale score of 2-4. The study subjects were evaluated for disease-associated severity according to symptoms, such as pain, mobility, daily active life, and functions using the arthritis society established specific measurement tool WOMAC score (Western Ontario and McMaster Universities Osteoarthritis Index). PPX treatment was given to these patients at baseline and once more at week 6 by either IV or IA administration.

Figure 5A:
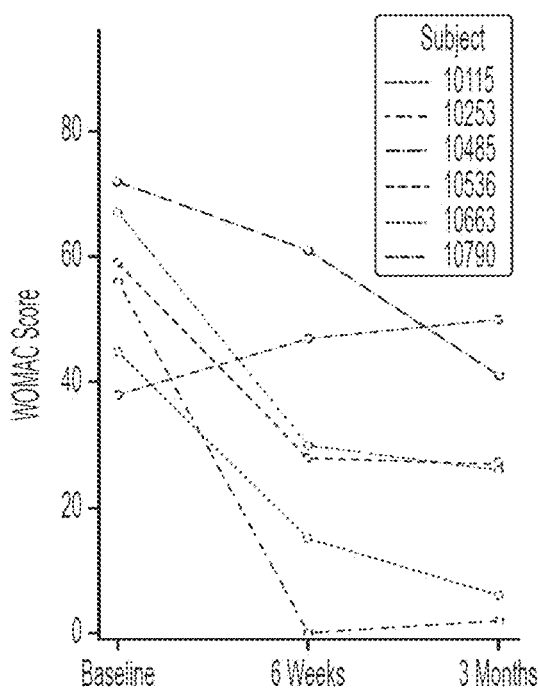
FIGS. 5A-5B present exemplary results of WOMAC scores in a set of subjects suffering from osteoarthritis treated with PPX.
Figure 5B:
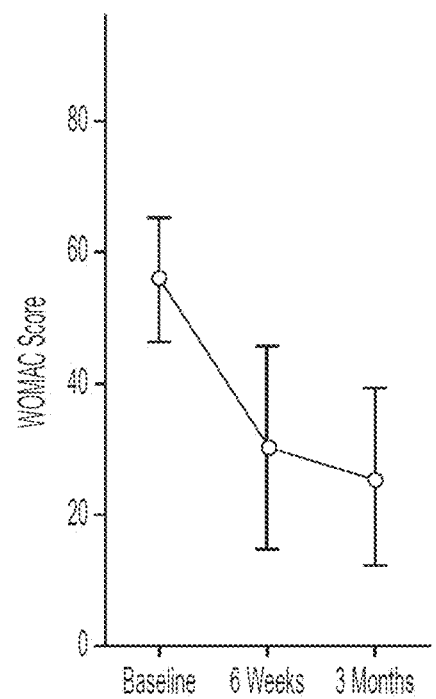
Figure 6A:
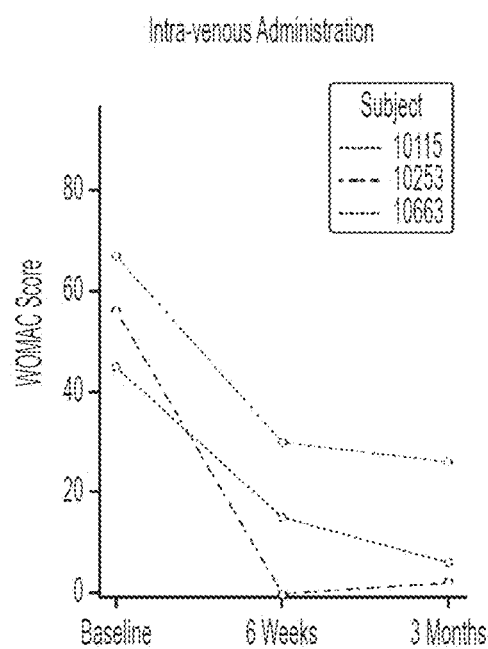
FIG. 6A-6B present exemplary results of WOMAC scores in a set of subjects suffering from osteoarthritis treated with PPX as shown in FIG. 5, grouped by route of administration.
Figure 6B:
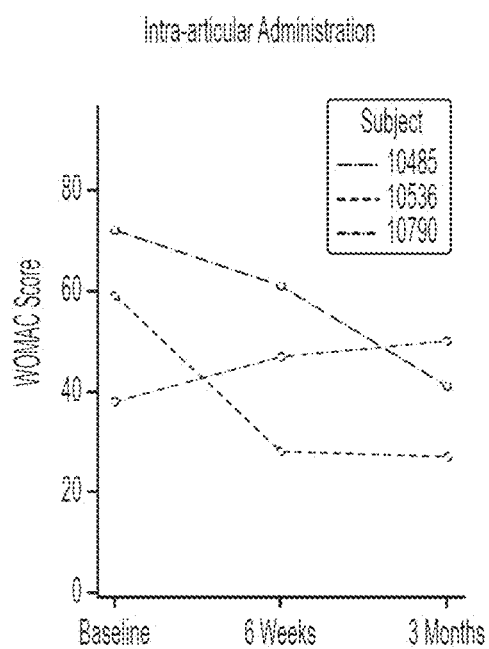

Six patients (3 IV and 3 IA treated subjects) enrolled in the study had completed the baseline, 6 week, and 3 month follow ups. At each timepoint, WOMAC scores were calculated to measure the severity of disease associated symptoms in each subject (FIG. 5A). Combing all subjects, WOMAC scores at each respective time point showed a trend for progressive decline in WOMAC score over time (FIG. 5B), indicating a general improvement in osteoarthritis symptoms after PPX treatment. A breakdown of WOMAC score data by PPX route of administration showed that all patients treated with PPX by IV had improved WOMAC scores by 3 months compared to baseline (FIG. 6A). Similarly, 2 out of the 3 patients treated with PPX by IA administration had improved WOMAC scores by 3 months compared to baseline (FIG. 6B). These results suggest that PPX is associated with positive improvements in Osteoarthritis associated symptoms.

Example 4—Therapeutic Dose of PPX

Two doses of PPX with nanoparticle concentrations of approximately 100 billion particles per mL can be administered to the patient to manage joint pain. One dose of PPX is a 1 mL total volume product that is stored frozen. When the product is thawed, the 1 mL dose is diluted in 100 mL saline for intravenous infusion or diluted in 1 mL of saline for local injection into the site.

Example Implementations

Item 1. A composition comprising proteinaceous blood-derived nanoparticles, wherein the nanoparticles have a diameter less than 200 nm.

Item 2. The composition of item 1, wherein the nanoparticles are extracellular vesicles (EVs).

Item 3. The composition of item 2, wherein the extracellular vesicles are autologous to the subject.

Item 4. The composition of item 2, wherein the extracellular vesicles are heterologous to the subject.

Item 5. The composition as in any one of items 1-4, wherein the extracellular vesicles comprise exosomes.

Item 6. The composition as in any one of items 1-5, wherein the extracellular vesicles comprise any of the surface-bound proteins CD41a, CD9, CD63, or CD81.

Item 7. The composition of item 6, wherein the concentration of EVs comprising CD41a is at least 109 EVs per mL.

Item 8. The composition of item 5, wherein the concentration of EVs comprising CD41a ranges from $10^9$ to $10^{13}$ EVs per mL.

Item 9. The composition as in any one of items 1-8, wherein a protein concentration is at least 2 mg/mL.

Item 10. The composition as in any one of items 1-8, wherein a protein concentration ranges from 2 to 10 mg/mL.

Item 11. The composition as in any one of items 1-8, wherein a protein concentration is about 4.5 mg/mL.

Item 12. The composition as in any one of items 1-11, wherein the diameter of the nanoparticles ranges from 20 nm to 200 nm.

Item 13. The composition as in any one of items 1-11, wherein the diameter of the nanoparticles is, on average, 60 nm.

Item 14. The composition as in any one of items 1-13, wherein the concentration of the nanoparticles ranges from $1.0 \times 10^{10}$ to $1.0 \times 10^{13}$ particles/mL.

Item 15. The composition as in any one of items 1-13, wherein the concentration of nanoparticles is about $3.0 \times 10^{11}$.

Item 16. A method of treating a disease or disorder in a subject in need thereof, comprising administering to the subject having the disease or disorder a therapeutically effective amount of a composition comprising blood-derived nanoparticles, the nanoparticles having a diameter less than 200 nm and a concentration of nanoparticles in the composition being at least $1 \times 10^8$ nanoparticles/ml.

Item 17. The method of item 16, wherein the composition is made by a process comprising:
(a) obtaining a volume of blood;
(b) centrifuging the volume of blood at 2,000×g for at least 10 minutes (min) to obtain a first supernatant;
(c) centrifuging the first supernatant at 100,000×g for at least 90 min to obtain a pellet comprising the nanoparticles;
(d) isolating and resuspending the pellet in a volume of resuspension fluid to obtain a resuspended volume; and
(e) filtering at least a portion of the resuspended volume using a 0.22 uM filter.

Item 18. The method of item 16, wherein the composition is made by a process comprising:
(a) obtaining a volume of blood;
(b) centrifuging the volume of blood at 2,000×g for at least 10 minutes (min) to obtain a first supernatant;
(c) centrifuging the first supernatant at 2,000×g for at least 5 min to obtain a second supernatant;
(d) centrifuging the second supernatant at 100,000×g for at least 90 min to obtain a pellet comprising the nanoparticles;
(e) isolating and resuspending the pellet in a volume of resuspension fluid to obtain a resuspended volume; and
(f) filtering at least a portion of the resuspended volume using a 0.22 uM filter.

Item 19. The method as in any one of items 16-18, wherein the disease or disorder is joint pain.

Item 20. The method of item 19, wherein the joint pain is derived from arthritis.

Item 21. The method of item 20, wherein the arthritis is osteoarthritis or rheumatoid arthritis.

Item 22. The method as in any one of items 19-21, wherein the joint is selected from the group consisting of hand, hip, shoulder, and knee.

Item 23. The method as in any one of items 16-22, wherein the nanoparticles are extracellular vesicles (EVs).

Item 24. The method of item 23, wherein the extracellular vesicles are autologous to the subject.

Item 25. The method of item 23, wherein the extracellular vesicles are heterologous to the subject.

Item 26. The method as in any one of items 23-25, wherein the extracellular vesicles comprise exosomes.

Item 27. The method as in any one of items 23-26, wherein the extracellular vesicles comprise any of the surface-bound proteins CD41a, CD9, CD63, or CD81.

Item 28. The method of item 27, wherein the concentration of EVs comprising CD41a is at least 107 EVs per mL.

Item 29. The method of item 27, wherein the concentration of EVs comprising CD41a ranges from $10^9$ to $10^{13}$ EVs per mL.

Item 30. The method as in any one of items 16-29, wherein a protein concentration is at least 0.02 mg/mL.

Item 31. The method as in any one of items 16-29, wherein a protein concentration ranges from 0.02 to 10 mg/mL.

Item 32. The method of item 31, wherein the protein concentration is about 0.045 mg/mL, 2.25 mg/mL, or 4.5 mg/mL.

Item 33. The method as in any one of items 16-32, wherein the diameter of the nanoparticles ranges from 20 nm to 200 nm.

Item 34. The method as in any one of items 16-32, wherein the diameter of the nanoparticles is, on average, 60 nm.

Item 35. The method as in any one of items 16-34, wherein the concentration of the nanoparticles is at least $10^9$ particles/mL.

Item 36. The method of item 35, wherein the concentration of the nanoparticles is at least $1.0 \times 10^{11}$ particles/mL.

Item 37. The method as in any one of items 16-34, wherein the concentration of nanoparticles ranges from $1.0 \times 10^8$ particles/mL to $1.0 \times 10^{13}$ particles/mL.

Item 38. The method as in any one of items 16-34, wherein the concentration of nanoparticles is about $3.0 \times 10^9$, $1.5 \times 10^{11}$, or $3.0 \times 10^{11}$ particles per mL.

Item 39. The method as in any one of items 16-38, wherein the wherein the composition is administered by intravenous or intraarticular injection.

Item 40. The method as in any one of items 16-39, wherein the subject is human.

Item 41. The method as in any one of items 16-40, wherein the subject is administered at least one dose of the composition.

Item 42. The method of item 41, wherein the subject is administered two doses of the composition.

Item 43. The method as in any one of items 16-23, wherein the nanoparticles are derived from the blood of the subject.

Item 44. The method of item 39, wherein the volume of the composition administered by intravenous injection is about 100 mL.

Item 45. The method of item 39, wherein the volume of the composition administered by intravenous injection is at least 100 mL.

1 Item 46. The method of item 39, wherein the volume of the composition administered by intravenous injection is 101 mL.

Item 47. The method of item 39, wherein the volume of the composition administered by intraarticular injection is about 1 mL or 2 mL.

Item 48. The method of item 39, wherein the volume of the composition administered by intraarticular injection is at least 1 mL or 2 mL.

Item 49. The method of item 39, wherein the volume of the composition administered by intraarticular injection is 1 mL or 2 mL.

REFERENCES

1. Bellio, M. A., et al., Amniotic fluid-derived extracellular vesicles: characterization and therapeutic efficacy in an experimental model of bronchopulmonary dysplasia. Cytotherapy, 2021.
2. Nie, L. Y., et al., Effectiveness of Platelet-Rich Plasma in the Treatment of Knee Osteoarthritis: A Meta-analysis of Randomized Controlled Clinical Trials. Orthop J Sports Med, 2021. 9(3): 2325967120973284.
3. Daaboul, G. G., et al., Digital Detection of Exosomes by Interferometric Imaging. Sci Rep, 2016. 6: 37246.

The entirety of each patent, patent application, publication or any other reference or document cited herein is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used in this specification, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used in this specification, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The technology is generally described herein using affirmative language to describe the numerous embodiments and aspects. The technology also specifically includes embodiments in which particular subject matter is excluded, in full or in part, such as substances or materials, method steps and conditions, protocols, or procedures. For example, in certain implementations or aspects of the technology, materials and/or method steps are excluded. Thus, even though the technology is generally not expressed herein in terms of what the technology does not include aspects that are not expressly excluded in the technology are nevertheless disclosed herein.

Some implementations of the technology described herein suitably can be practiced in the absence of an element not specifically disclosed herein. Accordingly, in some implementations, the term "including" or "includes" can be replaced with "consisting essentially of" or "consisting of" or grammatical variations thereof. The term "a" or "an" can refer to one of or a plurality of the elements it modifies (e.g., "a reagent" can mean one or more reagents) unless it is contextually clear either one of the elements or more than one of the elements is described. The term "about" as used in this specification refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used in this specification refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

What is claimed is:

1. A method of treating a disease or disorder in a subject in need thereof, the method comprising:
   administering to the subject having the disease or disorder a therapeutically effective amount of a composition comprising:
   blood-derived nanoparticles, the blood-derived nanoparticles having a diameter less than 200 nm, the blood-derived nanoparticles derived from substantially platelet-free and cell-free blood, and
   a concentration of blood-derived nanoparticles in the composition being at least $1 \times 10^8$ nanoparticles/ml.

2. The method of claim 1, wherein the composition is made by a process comprising:
(a) obtaining a volume of blood;
(b) centrifuging the volume of blood at 2,000×g for at least 10 minutes (min) to obtain a first supernatant;
(c) centrifuging the first supernatant at 100,000×g for at least 90 min to obtain a pellet comprising the nanoparticles;
(d) isolating and resuspending the pellet in a volume of resuspension fluid to obtain a resuspended volume; and
(e) filtering at least a portion of the resuspended volume using a 0.22 uM filter.

3. The method of claim 1, wherein the composition is made by a process comprising:
(a) obtaining a volume of blood;
(b) centrifuging the volume of blood at 2,000×g for at least 10 minutes (min) to obtain a first supernatant;
(c) centrifuging the first supernatant at 2,000×g for at least 5 min to obtain a second supernatant;
(d) centrifuging the second supernatant at 100,000×g for at least 90 min to obtain a pellet comprising the nanoparticles;
(e) isolating and resuspending the pellet in a volume of resuspension fluid to obtain a resuspended volume; and
(f) filtering at least a portion of the resuspended volume using a 0.22 uM filter.

4. The method of claim 1, wherein the disease or disorder is joint pain.

5. The method of claim 4, wherein the joint pain is derived from arthritis.

6. The method of claim 5, wherein the arthritis is osteoarthritis or rheumatoid arthritis.

7. The method of claim 4, wherein the joint is selected from the group consisting of hand, hip, shoulder, and knee.

8. The method of claim 1, wherein the nanoparticles are extracellular vesicles (EVs).

9. The method of claim 8, wherein the extracellular vesicles are autologous to the subject.

10. The method of claim 8, wherein the extracellular vesicles are heterologous to the subject.

11. The method of claim 8, wherein the extracellular vesicles comprise exosomes.

12. The method of claim 8, wherein the extracellular vesicles comprise any of the surface-bound proteins CD41a, CD9, CD63, or CD81.

13. The method of claim 12, wherein the concentration of EVs comprising CD41a is at least $10^7$ EVs per mL.

14. The method of claim 12, wherein the concentration of EVs comprising CD41a ranges from $10^9$ to $10^{13}$ EVs per mL.

15. The method of claim 1, wherein a protein concentration is at least 0.02 mg/mL.

16. The method of claim 1, wherein a protein concentration ranges from 0.02 to 10 mg/mL.

17. The method of claim 16, wherein the protein concentration is about 0.045 mg/mL, 2.25 mg/mL, or 4.5 mg/mL.

18. The method of claim 1, wherein the diameter of the nanoparticles ranges from 20 nm to 200 nm.

19. The method of claim 1, wherein the diameter of the nanoparticles is, on average, 60 nm.

20. The method of claim 1, wherein the concentration of the nanoparticles is at least $10^9$ particles/mL.

21. The method of claim 20, wherein the concentration of the nanoparticles is at least $1.0×10^{11}$ particles/mL.

22. The method of claim 1, wherein the concentration of nanoparticles ranges from $1.0×10^8$ particles/mL to $1.0×10^{13}$ particles/mL.

23. The method of claim 1, wherein the concentration of nanoparticles is about $3.0×10^9$, $1.5×10^{11}$, or $3.0×10^{11}$ particles per mL.

24. The method of claim 1, wherein the wherein the composition is administered by intravenous or intraarticular injection.

25. The method of claim 1, wherein the subject is administered at least one dose of the composition.

26. The method of claim 25, wherein the subject is administered two doses of the composition.

27. The method of claim 1, wherein the nanoparticles are derived from the blood of the subject.

28. The method of claim 24, wherein the volume of the composition administered by intravenous injection is at least 100 mL.

29. The method of claim 24, wherein the volume of the composition administered by intraarticular injection is about 1 mL or 2 mL.

30. The method of claim 24, wherein the volume of the composition administered by intraarticular injection is at least 1 mL.

* * * * *